(12) United States Patent
Tadaoka et al.

(10) Patent No.: US 10,562,919 B2
(45) Date of Patent: *Feb. 18, 2020

(54) COMPLEX AND PROCESS FOR PREPARING COMPLEX

(71) Applicant: SUMITOMO RUBBER INDUSTRIES, LTD., Kobe-shi, Hyogo (JP)

(72) Inventors: Hiroshi Tadaoka, Kobe (JP); Kazuyoshi Shiga, Kobe (JP)

(73) Assignee: SUMITOMO RUBBER INDUSTRIES, LTD., Kobe-Shi, Hyogo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/850,954

(22) Filed: Dec. 21, 2017

(65) Prior Publication Data

US 2018/0179230 A1 Jun. 28, 2018

(30) Foreign Application Priority Data

Dec. 22, 2016 (JP) ................................. 2016-250052
Jun. 30, 2017 (JP) ................................. 2017-129264

(51) Int. Cl.
C07F 3/06 (2006.01)
C07F 3/00 (2006.01)

(52) U.S. Cl.
CPC ............... C07F 3/06 (2013.01); C07F 3/003 (2013.01)

(58) Field of Classification Search
None
See application file for complete search history.

(56) References Cited

U.S. PATENT DOCUMENTS

2018/0178079 A1* 6/2018 Tadaoka ............. A63B 37/0059

FOREIGN PATENT DOCUMENTS

JP 1-245859 A 10/1989

OTHER PUBLICATIONS

Gordon et al., "Preparation and properties of tetrazinc μ4-oxohexa-μ-carboxylates (basic zinc carboxylates)", Canadian Journal of Chemistry, 61, 1983, pp. 1218-1221.
New Experimental Chemical Lecture, Edition 1st, vol. 8th, pp. 986-987.
Ötvös et al., "Synthesis and Spectroscopic and Computational Characterization of Zn4O(Alicyclic or Aromatic Carboxylate)6 Complexes as Potential MOF Precursors", Inorganic Chemistry, 2010, 49, pp. 4620-4625.

* cited by examiner

Primary Examiner — Clinton A Brooks
(74) Attorney, Agent, or Firm — Birch, Stewart, Kolasch & Birch LLP

(57) ABSTRACT

An object of the present invention is to provide a novel complex having at least one carbon-carbon double bond and/or carbon-carbon triple bond. The present invention provides a complex represented by formula (1):

$$((RCOO)_8 M_5(OH)_2)_n \quad (1)$$

wherein in the formula (1), M is a metal atom, R is a hydrogen atom, an alkyl group having 1 to 18 carbon atoms, an alkenyl group having 2 to 18 carbon atoms or an alkynyl group having 2 to 18 carbon atoms, a plurality of R may be identical to or different from each other, at least one of R is the alkenyl group having 2 to 18 carbon atoms or the alkynyl group having 2 to 18 carbon atoms, and n is an integer of 1 or more.

11 Claims, 7 Drawing Sheets

COMPLEX AND PROCESS FOR PREPARING COMPLEX

FIELD OF THE INVENTION

The present invention relates to a complex, more specifically, a complex having a reactive functional group. Further, the present invention relates to a process of preparing a complex.

DESCRIPTION OF THE RELATED ART

Japanese Patent Publication No. H1-245859 A discloses a macro porous ion selective exchange resin obtained by a crosslinking polymerization of a well-defined polymerizable metal complex, wherein the macro porous ion selective exchange resin is obtained by reacting a metal complex represented by a general formula of MaLbBcXd (1) with a monomer having at least two polymerizable carbon-carbon multiple bonds and/or an oligomer crosslinking agent (In the formula, M represents a main group metal and/or a sub group metal, L represents a polymerizable ligand, B represents a non-polymerizable ligand, X represents a non-polymerizable anion, a represents an integer of 1 to 6, b represents an integer of 1 to 8, c represents an integer of 0 to 4, and d represents an integer of 0 to 6.).

New Experimental Chemical Lecture, Edition 1$^{st}$, Volume 8$^{th}$, p. 986 discloses a process of preparing tetrazinc monoxide hexaacetate by heating zinc acetate (II) in vacuum.

Inorganic Chem. 2010, 49, 4620-4625 discloses a process of preparing $Zn_4O$ carboxylate by reacting a carboxylic acid with zinc oxide in carbon tetrachloride.

Can. J. Chem. 1983, 61, 1218 discloses a process of preparing a basic zinc 2-ethylhexanoate by reacting zinc oxide with zinc 2-ethylhexanoate in toluene.

SUMMARY OF THE INVENTION

An object of the present invention is to provide a novel complex having at least one carbon-carbon double bond and/or carbon-carbon triple bond. In addition, if a conventional preparing process is used to prepare the complex having at least one carbon-carbon double bond and/or carbon-carbon triple bond, there is a problem that the carbon-carbon double bonds and/or the carbon-carbon triple bonds are self-polymerized, thereby failing to obtain the target complex. The present invention has been made in view of the abovementioned circumstances, and an object of the present invention is to provide a novel preparing process of preparing a complex.

The present invention relates to a complex represented by a formula (1):

$$((RCOO)_8M_5(OH)_2)_n \qquad (1)$$

[In the formula (1), M is a metal atom, and R is a hydrogen atom, an alkyl group having 1 to 18 carbon atoms, an alkenyl group having 2 to 18 carbon atoms or an alkynyl group having 2 to 18 carbon atoms. A plurality of R may be identical to or different from each other, and at least one of R is the alkenyl group having 2 to 18 carbon atoms or the alkynyl group having 2 to 18 carbon atoms. n is an integer of 1 or more.].

The complex represented by the formula (1) is preferably a complex represented by a structural formula (2):

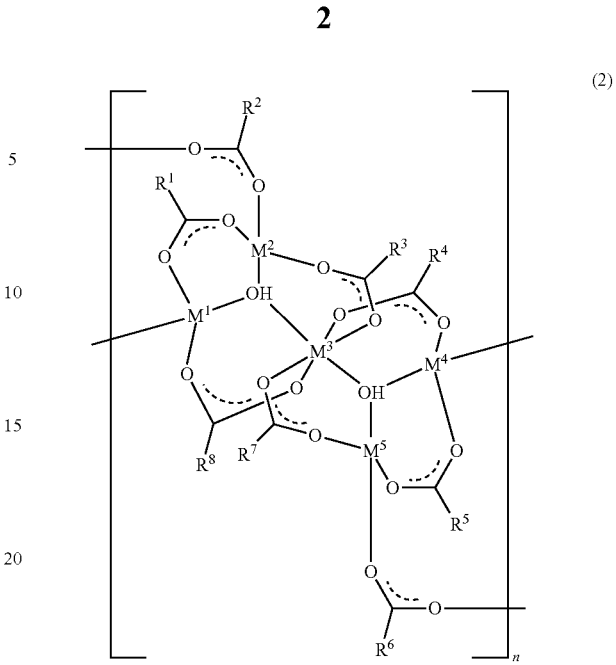

[In the structural formula (2), $M^1$ to $M^5$ are identical to or different from each other and represent a metal atom, $R^1$ to $R^8$ are identical to or different from each other and represent a hydrogen atom, an alkyl group having 1 to 18 carbon atoms, an alkenyl group having 2 to 18 carbon atoms or an alkynyl group having 2 to 18 carbon atoms, and at least one of $R^1$ to $R^8$ are the alkenyl group having 2 to 18 carbon atoms or the alkynyl group having 2 to 18 carbon atoms, n is an integer of 1 or more.].

The complex represented by a structural formula (2) (n=1 or more) is preferably a complex represented by a structural formula (3).

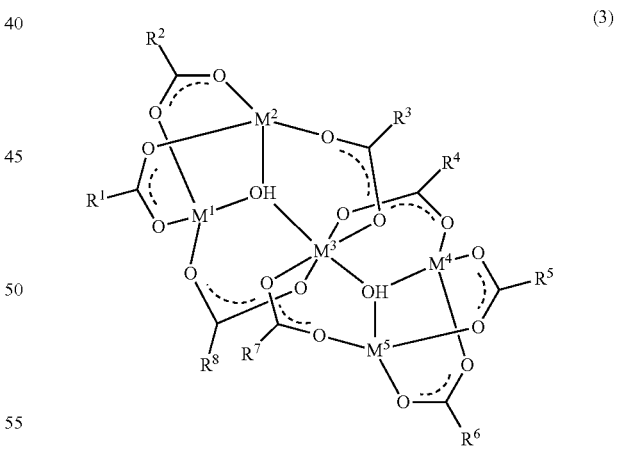

[In the formula (3), $M^1$ to $M^5$ are identical to or different from each other and represent a metal atom, $R^1$ to $R^8$ are identical to or different from each other and represent a hydrogen atom, an alkyl group having 1 to 18 carbon atoms, an alkenyl group having 2 to 18 carbon atoms or an alkynyl group having 2 to 18 carbon atoms, and at least one of $R^1$ to $R^8$ is the alkenyl group having 2 to 18 carbon atoms or the alkynyl group having 2 to 18 carbon atoms.].

The process for preparing a complex according to the present invention comprises a step of reacting a compound represented by a formula (4) with a metal oxide represented by a formula (5) in a solvent in the presence of water:

$$[M^6(RCOO)_x]\cdot yH_2O \quad (4)$$

$$M^7{}_aO_b \quad (5)$$

[In the formula (4), $M^6$ is a metal atom, R is a hydrogen atom, an alkyl group having 1 to 18 carbon atoms, an alkenyl group having 2 to 18 carbon atoms or an alkynyl group having 2 to 18 carbon atoms, x is a number corresponding to oxidation number of the metal atom $M^6$ and is an integer of 2 or more, y is an integer of 0 or more, and a plurality of R may be identical to or different from each other. In the formula (5), $M^7$ is a metal atom, a is an integer of 1 to 5, and b is an integer of 1 to 7.].

The process for preparing a complex according to the present invention comprises a step of reacting a compound represented by a formula (4) with a metal oxide represented by a formula (5) in a solvent to obtain a first complex, and a step of reacting the first complex with water to obtain a second complex:

$$[M^6(RCOO)_x]\cdot yH_2O \quad (4)$$

$$M^7{}_aO_b \quad (5)$$

[In the formula (4), $M^6$ is a metal atom, R is a hydrogen atom, an alkyl group having 1 to 18 carbon atoms, an alkenyl group having 2 to 18 carbon atoms or an alkynyl group having 2 to 18 carbon atoms, x is a number corresponding to oxidation number of the metal atom $M^6$ and is an integer of 2 or more, y is an integer of 0 or more, and a plurality of R may be identical to or different from each other. In the formula (5), $M^7$ is a metal atom, a is an integer of 1 to 5, and b is an integer of 1 to 7.].

The process for preparing a complex according to the present invention comprises a step of reacting a carboxylic acid represented by a formula (6) with a metal oxide represented by a formula (5) in a solvent:

$$RCOOH \quad (6)$$

$$M^7{}_aO_b \quad (5)$$

[In the formula (6), R is a hydrogen atom, an alkyl group having 1 to 18 carbon atoms, an alkenyl group having 2 to 18 carbon atoms or an alkynyl group having 2 to 18 carbon atoms. In the formula (5), $M^7$ is a metal atom, a is an integer of 1 to 5, and b is an integer of 1 to 7.].

According to the present invention, a novel complex having at least one carbon-carbon double bond and/or carbon-carbon triple bond is obtained. In addition, a novel preparing process of preparing a complex is provided.

DESCRIPTION OF THE PREFERRED EMBODIMENT

Figure 1:
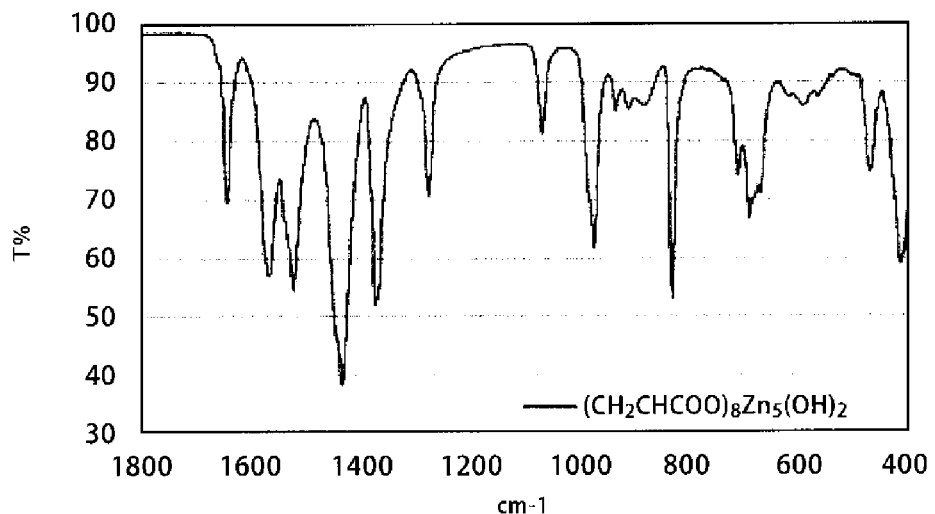
FIG. 1 shows IR spectrum of a preferable complex according to the present invention.

The present invention relates to a complex represented by a formula (1):

$$((RCOO)_8M_5(OH)_2)_n \quad (1)$$

[In the formula (1), M is a metal atom, OH is a hydroxyl group, RCOO is a carboxylate group, and R is a hydrogen atom, an alkyl group having 1 to 18 carbon atoms, an alkenyl group having 2 to 18 carbon atoms or an alkynyl group having 2 to 18 carbon atoms. A plurality of R may be identical to or different from each other, and at least one of R is the alkenyl group having 2 to 18 carbon atoms or the alkynyl group having 2 to 18 carbon atoms. n is an integer of 1 or more.].

A complex means a molecular compound having a metal atom or metal ion to which an atom or atomic group called a ligand is binding, and is also called a coordination compound.

Examples of the metal atom (M) include an alkali metal such as lithium, sodium, potassium, rubidium and cesium; an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; and a base metal such as beryllium, magnesium, aluminum, zinc, gallium, cadmium, indium, tin, thallium, lead, bismuth and polonium. These metal atoms may be used solely, or at least two of them may be used in combination. Among them, as the metal atom, the metal atom having oxidation number of +2 is preferable, and beryllium, magnesium, calcium, zinc, barium, nickel, cadmium or lead is more preferable. In the formula (1), a plurality of M are may be identical to or different from each other, and it is preferable that all of M are the same metal.

Examples of the alkyl group having 1 to 18 carbon atoms include methyl group, ethyl group, propyl group, butyl group, pentyl group, hexyl group, heptyl group, octyl group, nonyl group, decyl group, undecyl group, dodecylgroup, tridecyl group, tetradecyl group, pentadecyl group, hexadecyl group, heptadecyl group, and octadecyl group. The alkyl group having 1 to 18 carbon atoms may have a linear structure, a branched structure or a cyclic structure, and the linear structure is preferable.

Examples of the alkenyl group having 2 to 18 carbon atoms include ethenyl group (vinyl group), 1-propenyl group, 2-propenyl group, isopropenyl group, 3-butenyl group, 4-pentenyl group, 5-hexenyl group, 6-heptenyl group, 7-octenyl group, 8-nonenyl group, 9-decenyl group, 10-undecenyl group, 11-dodecenyl group, 8-tridecenyl group, 12-tridecenyl group, 13-tetradecenyl group, 8-pentadecenyl group, 14-pentadecenyl group, 15-hexadecenyl group, 8-heptadecenyl group, 10-heptadecenyl group, 16-heptadecenyl group, and 17-octadecenyl group. The alkenyl group having 2 to 18 carbon atoms may have a linear structure or a branched structure, and the linear structure is preferable. As the alkenyl group having 2 to 18 carbon atoms, an alkenyl group having one carbon-carbon double bond is preferable. The position of the carbon-carbon double bond is preferably α, β-position or a terminal of the alkenyl group. The alkenyl group preferably has 8 or less carbon atoms, more preferably 6 or less carbon atoms, and even more preferably 4 or less carbon atoms. Preferable examples of the alkenyl group having 2 to 18 carbon atoms include vinyl group, isopropenyl group, 1-propenyl group and 2-propenyl group.

Examples of the alkynyl group having 2 to 18 carbon atoms include ethynyl group, 1-propynyl group, 2-propynyl group, 3-butynyl group, 4-pentynyl group, 5-hexynyl group, 6-heptynyl group, 7-octynyl group, 8-nonynyl group, 9-decynyl group, 10-undecynyl group, 11-dodecynyl group, 8-tridecynyl group, 12-tridecynyl group, 13-tetradecynyl group, 8-pentadecynyl group, 14-pentadecynyl group, 15-hexadecynyl group, 8-heptadecynyl group, 10-heptadecynyl group, 16-heptadecynyl group, and 17-octadecynyl group. The alkynyl group having 2 to 18 carbon atoms may have a linear structure or a branched structure, and the linear structure is preferable. As the alkynyl group having 2 to 18 carbon atoms, an alkynyl group having one carbon-carbon triple bond is preferable. The position of the carbon-carbon triple bond is preferably α, β-position or a terminal of the alkynyl group. The alkynyl group preferably has 8 or less carbon atoms, more preferably has 6 or less carbon atoms, and even more preferably has 4 or less carbon atoms. Preferable examples of the alkynyl group having 2 to 18 carbon atoms include ethynyl group, 1-propynyl group and 2-propynyl group.

In the formula (1), at least one of R is the alkenyl group having 2 to 18 carbon atoms or the alkynyl group having 2 to 18 carbon atoms. In other words, the complex represented by the formula (1) has one or more carbon-carbon unsaturated bonds. The number of the alkenyl group having 2 to 18 carbon atoms or alkynyl group having 2 to 18 carbon atoms in the above R is preferably 3 or more, more preferably 4 or more, even more preferably 5 or more, and most preferably 8.

In the formula (1), at least one of R is preferably an alkenyl group having 2 to 18 carbon atoms and a carbon-carbon double bond at a terminal, or an alkynyl group having 2 to 18 carbon atoms and a carbon-carbon triple bond at a terminal. The number of the alkenyl group having 2 to 18 carbon atoms and a carbon-carbon double bond at a terminal or alkynyl group having 2 to 18 carbon atoms and having a carbon-carbon triple bond at a terminal in the above R is preferably 3 or more, more preferably 4 or more, even more preferably 5 or more, and most preferably 8.

In the formula (1), a plurality of R may be identical to or different from each other, and all of R are preferably the same group.

In the formula (1), a structure with n=1 is a basic structural unit of the complex. A complex having a structure with a plurality of the basic structural units (n is an integer of 2 or more) is also included in the present invention. The above n is an integer of 1 or more, and is preferably an integer of 2 or more. In an assembled complex (n is an integer of 2 or more), the upper limit of n is preferably, but not limited to, one hundred million, more preferably one million, and even more preferably ten thousands.

Examples of the complex represented by the formula (1) include a complex in which all the R are vinyl group and the metal atom (M) is zinc; and a complex in which all the R are isopropenyl group and the metal atom (M) is zinc.

The complex represented by the formula (1) is preferably a complex having a structure represented by a structural formula (2).

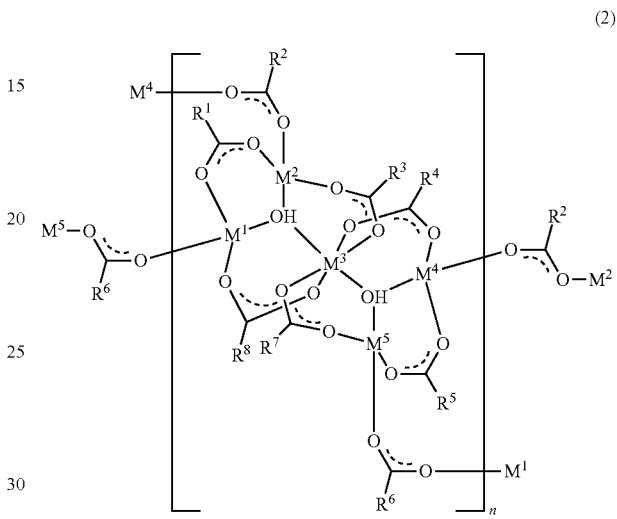

(2)

[In the formula (2), $M^1$ to $M^5$ are identical to or different from each other and represent a metal atom, O represents an oxygen atom, H represents a hydrogen atom, $R^1$ to $R^8$ are identical to or different from each other and represent a hydrogen atom, an alkyl group having 1 to 18 carbon atoms, an alkenyl group having 2 to 18 carbon atoms or an alkynyl group having 2 to 18 carbon atoms, n is an integer of 1 or more, and at least one of $R^1$ to $R^8$ is the alkenyl group having 2 to 18 carbon atoms or the alkynyl group having 2 to 18 carbon atoms.].

In the formula (2), the atomic group of the adjacent structural units is depicted outside the brackets. In the structural formula (2), the bond shown in the dashed line which is attached to the solid line is a hybrid bond of the carboxylate group. In addition, in the structural formula (2), the covalent bond and the coordination bond are both shown in a solid line.

In the formula (2), a complex in which n is 1 is a basic structural unit of the complex, and a complex in which n is an integer of 2 or more is an assembled complex formed by assembling the basic structural units. The above n is an integer of 1 or more, more preferably an integer of 2 or more. In the assembled complex (n is an integer of 2 or more), the upper limit of n is preferably, but not limited to, one hundred million, more preferably one million, and even more preferably ten thousand.

The assembled complex represented by the structural formula (2) has a three-dimensional structure represented by the following formulae (2-1) and (2-2). The formula (2-2) shows ORTEP (Oak Ridge Thermal-Ellipsoid Plot Program) of the crystal structure of the assembled complex. Based on these structural formulae, it is found that the assembled complex represented by the structural formula (2) has a three-dimensional structure in which four structural units bond to one structural unit.

In addition, the complex represented by the structural formula (2), (n is 1 or more) is preferably a complex represented by a formula (3) (n=1).

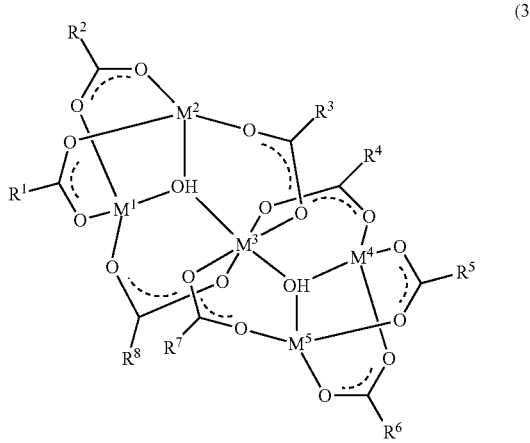

(3)

[In the formula (3), $M^1$ to $M^5$ are identical to or different from each other and represent a metal atom, O represents an oxygen atom, H represents a hydrogen atom, $R^1$ to $R^8$ are identical to or different from each other and represent a hydrogen atom, an alkyl group having 1 to 18 carbon atoms, an alkenyl group having 2 to 18 carbon atoms or an alkynyl group having 2 to 18 carbon atoms, and at least one of $R^1$ to $R^8$ is the alkenyl group having 2 to 18 carbon atoms or the alkynyl group having 2 to 18 carbon atoms.]

In the structural formula (3), the bond shown in the dashed line which is attached to the solid line is a hybrid bond of the carboxylate group. In addition, in the structural formula (3), the covalent bond and the coordination bond are both shown in a solid line.

The complex represented by the formula (3) is the basic structural unit. The assembled complex (n is an integer of 2 or more) in the formula (2) and the complex (n is 1) represented by the formula (3) exist in the solvent in an equilibrium state, and the existing proportion thereof varies depending on the solvent, temperature and concentration. The complex (n=1) represented by the formula (3) changes toward the assembled complex (n is an integer of 2 or more) which is more stable. For example, in a solid state, the assembled complex (n is an integer of 2 or more) which is more stable is obtained, and in a low concentration solution, the proportion of the complex represented by the formula (3) becomes high because it is stabilized by the solvent.

Examples of the metal atoms represented by $M^1$ to $M^5$ in the formulae (2) or (3) include those listed as M in the formula (1). Among them, as the metal atom, the metal atom having oxidation number of +2 is preferable, and beryllium, magnesium, calcium, zinc, barium, cadmium or lead is more preferable. The metal atoms represented by $M^1$ to $M^5$ may be different from each other, but are preferably all the same metal atom.

Examples of the alkyl group having 1 to 18 carbon atoms represented by $R^1$ to $R^8$ in the formulae (2) or (3) include those listed as R in the formula (1). The alkyl group having 1 to 18 carbon atoms may have a linear structure, a branched structure or a cyclic structure, and the linear structure is preferable.

Examples of the alkenyl group having 2 to 18 carbon atoms represented by $R^1$ to $R^8$ in the formulae (2) or (3) include those listed as R in the formula (1). The alkenyl group having 2 to 18 carbon atoms may have a linear structure or a branched structure, and the linear structure is preferable. As the alkenyl group having 2 to 18 carbon atoms, an alkenyl group having a carbon-carbon double bond at α, β-position or at a terminal thereof is preferable. The alkenyl group preferably has 8 or less carbon atoms, more preferably 6 or less carbon atoms, and even more preferably 4 or less carbon atoms. Preferable examples of the alkenyl group having 2 to 18 carbon atoms include vinyl group, isopropenyl group, 1-propenyl group and 2-propenyl group.

Examples of the alkynyl group having 2 to 18 carbon atoms represented by $R^1$ to $R^8$ in the formulae (2) or (3) include those listed as R in the formula (1). The alkynyl group having 2 to 18 carbon atoms may have a linear structure or a branched structure, and the linear structure is preferable. As the alkynyl group having 2 to 18 carbon atoms, an alkynyl group having a carbon-carbon triple bond at α, β-position or at a terminal thereof is preferable. The alkynyl group preferably has 8 or less carbon atoms, more preferably 6 or less carbon atoms, and even more preferably 4 or less carbon atoms. Preferable examples of the alkynyl group having 2 to 18 carbon atoms include ethynyl group, 1-propynyl group and 2-propynyl group.

In the formulae (2) or (3), at least one of $R^1$ to $R^8$ is the alkenyl group having 2 to 18 carbon atoms or the alkynyl group having 2 to 18 carbon atoms. The number of the alkenyl group having 2 to 18 carbon atoms or alkynyl group having 2 to 18 carbon atoms in the above $R^1$ to $R^8$ is preferably 2 or more, more preferably 4 or more, even more preferably 5 or more, particularly preferably 8.

In the formulae (2) or (3), at least one of $R^1$ to $R^8$ is preferably an alkenyl group having 2 to 18 carbon atoms and a carbon-carbon double bond at a terminal thereof, or an alkynyl group having 2 to 18 carbon atoms and a carbon-carbon triple bond at a terminal thereof. The number of the alkenyl group having 2 to 18 carbon atoms and a carbon-carbon double bond at a terminal thereof or alkynyl group having 2 to 18 carbon atoms and a carbon-carbon triple bond at a terminal thereof in the above $R^1$ to $R^8$ is preferably 3 or more, more preferably 4 or more, even more preferably 5 or more, particularly preferably 8.

In the formulae (2) or (3), $R^1$ to $R^8$ may be identical to or different from each other, and all of them are preferably the same.

In the formulae (2) or (3), $R^1$ to $R^8$ are a complex (zinc acrylate hydroxo cluster) in which all of $R^1$ to $R^8$ are vinyl group and the metal atoms ($M^1$ to $M^5$) is zinc; and a complex (zinc methacrylate hydroxo cluster) in which all of $R^1$ to $R^8$ are isopropenyl group and the metal atom ($M^1$ to $M^5$) is zinc.

The process for preparing a complex according to the present invention comprises a step of reacting a compound represented by a formula (4) with a metal oxide represented by a formula (5) in a solvent in the presence of water (first preparing process).

$$[M^6(RCOO)_x] \cdot yH_2O \quad (4)$$

$$M^7{}_aO_b \quad (5)$$

In addition, the process for preparing a complex according to the present invention may comprise a step of reacting a compound represented by the formula (4) with a metal oxide represented by the formula (5) in a solvent to obtain a first complex, and a step of reacting the first complex with water to obtain a second complex (second preparing process).

[In the formula (4), $M^6$ is a metal atom, R is a hydrogen atom, an alkyl group having 1 to 18 carbon atoms, an alkenyl group having 2 to 18 carbon atoms or an alkynyl group having 2 to 18 carbon atoms, x is a number corresponding to oxidation number of the metal atom $M^6$ and is an integer of 2 or more, y is an integer of 0 or more, and a plurality of R may be identical to or different from each other. In the formula (5), $M^7$ is a metal atom, a is an integer of 1 to 5, and b is an integer of 1 to 7.].

The present invention further includes a process for preparing a complex comprising a step of reacting a carboxylic acid represented by a formula (6) with a metal oxide represented by the formula (5) in a solvent (third preparing process).

RCOOH (6)

$M^7_aO_b$ (5)

[In the formula (6), R is a hydrogen atom, an alkyl group having 1 to 18 carbon atoms, an alkenyl group having 2 to 18 carbon atoms or an alkynyl group having 2 to 18 carbon atoms. In the formula (5), $M^7$ is a metal atom, a is an integer of 1 to 5, and b is an integer of 1 to 7.].

It is noted that, in the description of the present invention, the compound represented by the formula (4) is sometimes simply referred to as "compound (4)", the metal oxide represented by the formula (5) is sometimes simply referred to as "metal oxide (5)", and the carboxylic acid represented by the formula (6) is sometimes simply referred to as "carboxylic acid (6)". In addition, the step of reacting the compound represented by the formula (4) with the metal oxide represented by the formula (5) in the solvent to obtain the first complex is sometimes simply referred to as "first step", and the step of reacting the first complex with water to obtain the second complex is sometimes simply referred to as "second step".

The materials used in the process of preparing a complex according to the present invention will be firstly explained. R in the compound (4) is a hydrogen atom, an alkyl group having 1 to 18 carbon atoms, an alkenyl group having 2 to 18 carbon atoms, or an alkynyl group having 2 to 18 carbon atoms.

Examples of the alkyl group having 1 to 18 carbon atoms include methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, and octadecyl group. The alkyl group having 1 to 18 carbon atoms may have a linear structure, a branched structure or a cyclic structure, and the linear structure is preferable.

Examples of the alkenyl group having 2 to 18 carbon atoms include ethenyl group (vinyl group), 1-propenyl group, 2-propenyl group, isopropenyl group, butenyl group, pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, and octadecenyl group. The alkenyl group having 2 to 18 carbon atoms may have a linear structure or a branched structure, and the linear structure is preferable. As the alkenyl group having 2 to 18 carbon atoms, an alkenyl group having one carbon-carbon double bond is preferable. The position of the carbon-carbon double bond is preferable α, β-position or a terminal of the alkenyl group. The alkenyl group preferably has 8 or less carbon atoms, more preferably 6 or less carbon atoms, and even more preferably 4 or less carbon atoms. Preferable examples of the alkenyl group having 2 to 18 carbon atoms include vinyl group, isopropenyl group, 1-propenyl group and 2-propenyl group.

Examples of the alkynyl group having 2 to 18 carbon atoms include ethynyl group, 1-propynyl group, 2-propynyl group, butynyl group, pentynyl group, hexynyl group, heptynyl group, octynyl group, nonynyl group, decynyl group, undecynyl group, dodecynyl group, tridecynyl group, tetradecynyl group, pentadecynyl group, hexadecynyl group, heptadecynyl group, and octadecynyl group. The alkynyl group having 2 to 18 carbon atoms may have a linear structure or a branched structure, and the linear structure is preferable. As the alkynyl group having 2 to 18 carbon atoms, an alkynyl group having one carbon-carbon triple bond is preferable. The positon of the carbon-carbon triple bond is preferable α, β-position or a terminal of the alkynyl group. The alkynyl group preferably has 8 or less carbon atoms, more preferably 6 or less carbon atoms, and even more preferably 4 or less carbon atoms. Preferable examples of the alkynyl group having 2 to 18 carbon atoms include ethynyl group, 1-propynyl group and 2-propynyl group.

Examples of the metal atom ($M^6$) in the compound (4) include an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; and a base metal such as beryllium, magnesium, aluminum, zinc, gallium, cadmium, indium, tin, thallium, lead, bismuth and polonium. Among them, as the metal atom, the metal atom capable of forming a metal ion with bivalence or higher valence is preferable, and the metal atom capable of forming a divalent metal ion is more preferable. As the metal atom, at least one member selected from the group consisting of beryllium, magnesium, calcium, zinc, barium, cadmium and lead is preferable. These metal atoms may be used solely, or a mixture of at least two of them may be used.

x represents a number of the carboxylate groups (RCOO) in the compound (4). x is a number corresponding to oxidation number of the metal atom $M^6$, and is an integer of 2 or more. x is, for example, preferably 2 to 5, more preferably 2. y is an integer of 0 or more, and is, for example, preferably 0 to 5, more preferably 0. This is because if y is 1 or more, the yield of the target complex may be lowered.

Preferable specific examples of the compound (4) include a fatty acid metal salt. Examples of the fatty acid constituting the fatty acid metal salt include a saturated fatty acid having 1 to 19 carbon atoms, and an unsaturated fatty acid having 3 to 20 carbon atoms.

Examples of the saturated fatty acid include methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, and nonadecanoic acid. Examples of the unsaturated fatty acid include an unsaturated fatty acid having a carbon-carbon double bond such as propenoic acid (acrylic acid), 2-methylprop-2-enoic acid (methacrylic acid), 2-butenoic acid, 3-butenoic acid, 4-pentenoic acid, 5-hexenoic acid, 6-heptenoic acid, 7-octenoic acid, 8-nonenoic acid, 9-decenoic acid, 10-undecenoic acid, 11-dodecenoic acid, 12-tridecenoic acid, 9-tetradecenoic acid, 13-tetradecenoic acid, 14-pentadecenoic acid, 9-hexadecenoic acid, 15-hexadecenoic acid, 16-heptadecenoic acid, 9-octadecenoic acid, 11-octadecenoic acid, 17-octadecenoic acid and 18-nonadecenoic acid; and an unsaturated fatty acid having a carbon-carbon triple bond such as propiolic acid, 3-butynoic acid, 4-pentynoic acid, 5-hexynoic acid, 6-heptynoic acid, 7-octynoic acid, 8-nonynoic acid, 9-decynoic acid, 10-undecynoic acid, 11-dodecynoic acid, 12-tridecynoic acid, 9-tetradecynoic acid, 13-tetradecynoic acid, 14-pentadecynoic acid, 9-hexadecynoic acid, 15-hexadecynoic acid, 16-heptadecynoic acid, 9-octadecynoic acid, 11-octadecynoic acid, 17-octadecynoic acid, and 18-nonadecynoic acid.

As the unsaturated fatty acid having a carbon-carbon double bond, a fatty acid having one carbon-carbon double bond is preferable. The position of the carbon-carbon double bond is preferably α, β-position or a terminal of the unsaturated fatty acid. As the unsaturated fatty acid having a carbon-carbon triple bond, a fatty acid having one carbon-carbon triple bond is preferable. The position of the carbon-carbon triple bond is preferable α, β-position or a terminal of the unsaturated fatty acid.

Examples of the metal atom ($M^6$) of the fatty acid metal salt include an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; a base metal such as beryllium, magnesium, aluminum, zinc, gallium, cadmium, indium, tin, thallium, lead, bismuth and polonium. Among them, as the metal atom, the metal atom capable of forming a divalent metal ion is preferable, and beryllium, magnesium, calcium, zinc, barium, cadmium or lead is more preferable. These metal atoms may be used solely, or a mixture of at least two of them may be used.

As the fatty acid metal salt, the fatty acid metal salt in which the metal ion is a divalent metal ion is preferable, the unsaturated fatty acid metal salt in which the metal ion is a divalent metal ion is more preferable, and the acrylic acid metal salt or methacrylic acid metal salt in which the metal ion is a divalent metal ion is even more preferable.

In the preparing process according to the present invention, as the compound (4), zinc acrylate and/or zinc methacrylate is preferably used.

When two or more of the fatty acid metal salts are used in combination as the compound (4), the amount of each fatty acid metal salt can be suitably adjusted in accordance with the desired complex. The amount of the unsaturated fatty acid in the fatty acid constituting the compound (4) is preferably 33 mol % or more, more preferably 50 mol % or more, and even more preferably 66 mol % or more. It is also preferable that all the fatty acids constituting the compound (4) are the unsaturated fatty acid. In addition, the amount of the unsaturated fatty acid having a carbon-carbon double bond in the fatty acid constituting the compound (4) is preferably 33 mol % or more, more preferably 50 mol % or more, and even more preferably 66 mol % or more. It is also preferable that all the fatty acids constituting the compound (4) are the unsaturated fatty acid having a carbon-carbon double bond. As the fatty acid constituting the compound (4), a plurality of fatty acids may be used in combination, but one fatty acid is preferably used.

Examples of the embodiment of the fatty acid metal salt used as the compound (4) include an embodiment including one fatty acid and one metal ion; an embodiment including a plurality of fatty acids and one metal ion; an embodiment including one fatty acid and a plurality of metal ions; and an embodiment including a plurality of fatty acids and a plurality of metal ions. Among them, the embodiment including one fatty acid and one metal ion is preferable. The fatty acid metal salt may be used solely, or at least two of them may be used in combination.

In the preparing process according to the present invention, the metal oxide represented by the formula (5) is used.

$$M^7{}_aO_b \qquad (5)$$

Examples of the metal atom ($M^7$) include an alkali metal such as lithium, sodium, potassium, rubidium and cesium; an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; a base metal such as beryllium, magnesium, aluminum, zinc, gallium, cadmium, indium, tin, thallium, lead, bismuth and polonium. Among them, as the metal atom $M^7$, the metal atom capable of forming a divalent metal ion is preferable, and beryllium, magnesium, calcium, zinc, barium, cadmium or lead is more preferable. These metal atoms may be used solely, or a mixture of at least two of them may be used.

In the first preparing process and the second preparing process according to the present invention, the metal atom $M^6$ in the compound (4) and the metal atom $M^7$ in the metal oxide (5) may be identical to or different from each other, and are preferably identical to each other.

In the metal oxide (5), a is preferably an integer of 1 or more and 5 or less, more preferably an integer of 1 or more and 3 or less, and most preferably 1, and b is preferably an integer of 1 or more and 7 or less, more preferably an integer of 1 or more and 5 or less, even more preferably an integer of 1 or more and 3 or less, and most preferably 1. As the metal oxide (5), a divalent metal oxide with a=1 and b=1 is preferable.

Specific examples of the metal oxide (5) include an alkali metal oxide such as lithium oxide, sodium oxide, potassium oxide, rubidium oxide and cesium oxide; an alkaline earth metal oxide such as calcium oxide, strontium oxide and barium oxide; a transition metal oxide such as scandium oxide, titanium oxide, vanadium oxide, chromium oxide, manganese oxide, iron oxide, cobalt oxide, nickel oxide, copper oxide, yttrium oxide, zirconium oxide, niobium oxide, molybdenum oxide, technetium oxide, ruthenium oxide, rhodium oxide, palladium oxide, silver oxide, hafnium oxide, tantalum oxide, tungsten oxide, rhenium oxide, osmium oxide, iridium oxide, platinum oxide and gold oxide; and a base metal oxide such as beryllium oxide, magnesium oxide, aluminum oxide, zinc oxide, gallium oxide, cadmium oxide, indium oxide, tin oxide, thallium oxide, lead oxide, bismuth oxide and polonium oxide. These metal oxides may be used solely, or a mixture of at least two of them may be used. Among them, as the metal oxide, the divalent metal oxide is preferable, and beryllium oxide, magnesium oxide, calcium oxide, zinc oxide, barium oxide, cadmium oxide or lead oxide is more preferable. In the present invention, as the metal oxide (5), zinc oxide is most preferably used.

Examples of the solvent (hereinafter sometimes referred to as "first solvent") used in the reaction of the preparing process according to the present invention include, but are not limited to, dichloromethane, 1,2-dichloroethane, chloroform, chlorobenzene, dichlorobenzene, benzene, toluene, xylene, tetrahydrofuran, 1,4-dioxane, ethyl acetate, propyl acetate, isopropyl acetate, and acetonitrile. Examples of the solvent used in the reaction of the second preparing process further include alcohols such as methanol, ethanol, propanol and isopropanol. From the viewpoint of enhancing the yield of the complex, dichloromethane is preferably used as the solvent.

The first preparing process according to the present invention comprises a step of reacting the compound represented by the formula (4) with the metal oxide represented by the formula (5) in the solvent in the presence of water. In addition, the second preparing process according to the present invention comprises a step of reacting the compound represented by the formula (4) with the metal oxide represented by the formula (5) in the solvent (preferably in a solvent not containing water) to obtain the first complex, and a step of reacting the first complex with water to obtain the second complex.

The reaction of the compound (4) with the metal oxide (5) is carried out, for example, by dissolving or dispersing the compound (4) and the metal oxide (5) in the first solvent, and stirring the resultant reaction liquid.

Specifically, firstly, the metal oxide (5) is dissolved or dispersed in a solvent in a reaction vessel. While stirring the liquid obtained by dissolving or dispersing the metal oxide (5) in the solvent, a liquid obtained by dissolving or dispersing the compound (4) in a solvent is added therein. The liquid obtained by dissolving or dispersing the compound (4) in the solvent may be added dropwise therein. In this case, the dropwise addition time is preferably, but not limited to, 0.5 hour to 3 hours. The reaction is preferably carried out while further stirring the reaction liquid after the dropwise addition.

In the first preparing process according to the present invention, when the reaction is carried out in the solvent in the presence of water, the amount of water existing in the reaction system is preferably 1 part by mass or more, more preferably 2 parts by mass or more, and even more preferably 3 parts by mass or more, and is preferably 1000 parts by mass or less, more preferably 900 parts by mass or less, and even more preferably 800 parts by mass or less, with respect to 100 parts by mass of a total amount of the compound (4) and the metal oxide (5). This is because if the amount of water falls within the above range, the complex is obtained in a good yield and the operation does not become cumbersome. It is noted that water may be added in the reaction vessel as is done for the compound (4) or the metal oxide (5).

In the second preparing process according to the present invention, when the compound (4) and the metal oxide (5) are reacted, the reaction is preferably carried out under a condition that substantially no water exists in the reaction system. Thus, the reaction is preferably carried out in an inert gas atmosphere such as argon and nitrogen.

In the reaction of the compound (4) with the metal oxide (5), the molar ratio ((4)/(5)) of the compound (4) to the metal oxide (5) is preferably 3/2 or more, more preferably 2/1 or more, and is preferably 5/1 or less, more preferably 4/1 or less. This is because if the molar ratio ((4)/(5)) of the compound (4) to the metal oxide (5) falls within the above range, the yield of the obtained complex is higher.

In addition, the amount of the solvent in the reaction is preferably 1000 parts by mass or more, more preferably 2000 parts by mass or more, and even more preferably 3000 parts by mass or more, and is preferably 10000 parts by mass or less, more preferably 8000 parts by mass or less, and even more preferably 6000 parts by mass or less, with respect to 100 parts by mass of a total amount of the compound (4) and the metal oxide (5). If the amount of the solvent exceeds 10000 parts by mass, the synthetic workload increases, and if the amount of the solvent is less than 1000 parts by mass, the yield of the complex may be lowered.

The reaction temperature (temperature of the reaction liquid) is preferably −20° C. or more, more preferably 0° C. or more, even more preferably 10° C. or more, and most preferably 20° C. or more, and is preferably 100° C. or less, more preferably 90° C. or less, even more preferably 80° C. or less, and most preferably 50° C. or less. If the reaction temperature is −20° C. or more, the reaction speed between the compound (4) and the metal oxide (5) can be enhanced. In addition, if the reaction temperature is 100° C. or less, the self-polymerization of the compound (4) can be prevented.

The reaction time is preferably 1 hour or more, more preferably 2 hours or more, and even more preferably 3 hours or more. This is because if the reaction time is too short, the yield of the complex may be lowered. In addition, from the viewpoint of enhancing the productivity, the reaction time is preferably 300 hours or less, more preferably 200 hours or less, and even more preferably 100 hours or less. It is noted that the end of the reaction can be confirmed, for example, by a method of measuring the infrared absorption of a sample taken from the reaction liquid, or by a method of measuring the change in the weight or the like of the component dissolved in the reaction liquid.

In the first preparing process according to the present invention, the compound (4) and the metal oxide (5) are reacted in the presence of water to obtain the target complex. In the second preparing process according to the present invention, the compound (4) and the metal oxide (5) are reacted to obtain an intermediate, i.e. the first complex, and then the first complex and water are reacted to obtain the second complex (target complex).

In the second preparing process according to the present invention, the first complex obtained as the intermediate is a complex represented by the following formula (7), and preferably a complex represented by the following structural formula (8):

$$[M_4O(RCOO)_6]_n \quad (7)$$

[In the formula (7), M is a metal atom, and R is a hydrogen atom, an alkyl group having 1 to 18 carbon atoms, an alkenyl group having 2 to 18 carbon atoms or an alkynyl group having 2 to 18 carbon atoms. In the formula (7), a plurality of R may be identical to or different from each other, at least one of R is the alkenyl group having 2 to 18 carbon atoms or the alkynyl group having 2 to 18 carbon atoms, and n is an integer of 1 or more, preferably 1 to 8.].

Specific examples of the metal atom M and R in the formula (7) include those listed in the formula (1).

Examples of the first complex represented by the formula (7) include a complex in which all the R are vinyl group and the metal atom (M) is zinc; and a complex in which all the R are isopropenyl group and the metal atom (M) is zinc.

The complex represented by the formula (7) is preferably the complex represented by the structural formula (8):

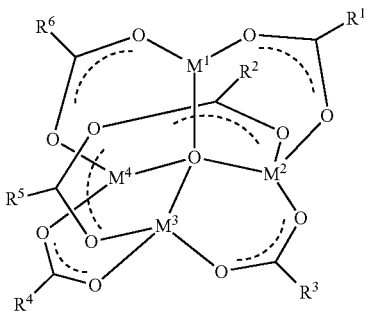

(8)

[In the structural formula (8), $M^1$ to $M^4$ are identical to or different from each other and represent a metal atom, $R^1$ to $R^6$ are identical to or different from each other and represent a hydrogen atom, an alkyl group having 1 to 18 carbon atoms, an alkenyl group having 2 to 18 carbon atoms or an alkynyl group having 2 to 18 carbon atoms, and at least one of $R^1$ to $R^6$ are the alkenyl group having 2 to 18 carbon atoms or the alkynyl group having 2 to 18 carbon atoms.].

In the structural formula (8), the bond shown in the dashed line which is attached to the solid line is a hybrid bond of the carboxylate group. In addition, in the structural formula (8), the covalent bond and the coordination bond are both shown in a solid line.

Specific examples of the metal atoms $M^1$ to $M^4$ and $R^1$ to $R^6$ in the structural formula (8) include those listed in the structural formula (2).

Preferable examples of the first complex include a complex (zinc acrylate oxo cluster) in which $M^1$ to $M^4$ are zinc and $R^1$ to $R^6$ are —CH=$CH_2$ in the structural formula (8); and a complex (zinc methacrylate oxo cluster) in which $M^1$ to $M^4$ are zinc and $R^1$ to $R^6$ are —$C(CH_3)$=$CH_2$ in the structural formula (8).

The first preparing process according to the present invention preferably comprises an insoluble substance removal step, a precipitation step, a recovery step or a purification step, after the reaction of the compound (4) with the metal oxide (5) is ended. The insoluble substance removal step, precipitation step, recovery step and purification step can be suitably combined where necessary.

(Insoluble Substance Removal Step)

After the reaction is ended, the insoluble substance is removed from the reaction liquid. Examples of the insoluble substance include unreacted raw materials, and the self-polymerized polymer of the compound (4). Examples of the method of removing the insoluble substance include, but are not limited to, a method of filtering the reaction liquid.

(Precipitation Step)

In the precipitation step, a second solvent is charged into the reaction liquid from which the insoluble substance has been removed to precipitate the target complex dissolved in the first solvent (solvent used for the reaction). The reaction liquid contains the target complex, and, for example, the unreacted compound (4). If the solubility of the target complex in the second solvent is lower than the solubility of the compound (4) in the second solvent, the target complex can be selectively precipitated. The second solvent is not particularly limited, as long as it can selectively precipitate the target complex in the reaction liquid. Examples of the second solvent include hydrocarbons such as hexane, pentane, cyclohexane and heptane.

The amount of the second solvent may be suitably adjusted such that the target complex can be precipitated. The amount of the second solvent is preferably 10 parts by mass or more, more preferably 20 parts by mass or more, and even more preferably 30 parts by mass or more, and is preferably 200 parts by mass or less, more preferably 150 parts by mass or less, and even more preferably 100 parts by mass or less, with respect to 100 parts by mass of the amount of the first solvent.

In addition, after the second solvent is charged, a part of the first solvent and second solvent may be removed to precipitate the target complex. As the method of removing a part of the first solvent and second solvent, concentration under reduced pressure is preferable. When performing the concentration under reduced pressure, the reaction liquid may be heated. The temperature of the reaction liquid when performing the concentration is preferably 100° C. or less, more preferably 80° C. or less, and even more preferably 60° C. or less.

The precipitated target complex is filtered and dried.

(Recovery Step)

In the recovery step, the solvent is removed from the reaction liquid from which the insoluble substance has been removed. The target complex existing in the reaction liquid can be recovered by removing the solvent.

Examples of the method of removing the solvent include a method of drying under reduced pressure and a method of drying under heating, and the drying under reduced pressure is preferable. When performing the drying under reduced pressure, the reaction liquid may be heated. The temperature of the reaction liquid when performing the drying is preferably 100° C. or less, more preferably 80° C. or less, and even more preferably 60° C. or less.

(Purification Step)

In the purification step, the purity of the target complex can be increased by reprecipitating the target complex obtained in the precipitation step or the recovery step. Specifically, after the obtained target complex is dissolved in the first solvent, the second solvent is charged into the first solvent in which the target complex is dissolved to precipitate the target complex, and the target complex is recovered.

Examples of the first solvent and the second solvent used in the purification step include those listed in the above reaction step and precipitation step. In addition, the preferable amount of the second solvent is also same as that in the above precipitation step. The purification step may be performed several times depending on the desired purity of the target complex.

The second preparing process according to the present invention preferably comprises an insoluble substance removal step, a recovery step, a precipitation step or a purification step, after the reaction of the compound (4) with the metal oxide (5) is ended. The insoluble substance removal step, recovery step, precipitation step and purification step can be suitably combined where necessary.

(Insoluble Substance Removal Step)

After the reaction is ended, the insoluble substance is removed from the reaction liquid. Examples of the insoluble substance include unreacted raw materials, and the self-polymerized polymer of the compound (4). Examples of the method of removing the insoluble substance include, but are not limited to, a method of filtering the reaction liquid.

(Recovery Step)

In the recovery step, the solvent is removed from the reaction liquid from which the insoluble substance has been removed. A mixture containing the compound (4) and the generated first complex is obtained by removing the solvent.

Examples of the method of removing the solvent include a method of drying under reduced pressure and a method of drying under heating, and the drying under reduced pressure is preferable. When performing the drying under reduced pressure, the reaction liquid may be heated. The temperature of the reaction liquid when performing the drying is preferably 100° C. or less, more preferably 80° C. or less, and even more preferably 60° C. or less.

In the second preparing process according to the present invention, the following precipitation step may be performed before the recovery step. The purity of the first complex contained in the reaction liquid can be increased by performing the precipitation step.

(Precipitation Step)

In the precipitation step, a second solvent is charged into the reaction liquid from which the insoluble substance has been removed in the reaction step, and the resultant precipitate is removed. Raw materials, by-products and the like dissolved in the first solvent are precipitated by charging the second solvent into the reaction liquid. The purity of the first complex contained in the reaction liquid can be increased by removing the precipitate.

The second solvent is not particularly limited, as long as it can selectively precipitate the compound (4) in the reaction liquid. In other words, the solubility of the first complex in the second solvent is higher than the solubility of the compound (4) in the second solvent. Examples of the second solvent include hydrocarbons such as hexane, pentane, cyclohexane and heptane.

The amount of the second solvent may be suitably adjusted such that the compound (4) can be precipitated. The amount of the second solvent is preferably 10 parts by mass or more, more preferably 20 parts by mass or more, and even more preferably 30 parts by mass or more, and is preferably 200 parts by mass or less, more preferably 150 parts by mass or less, and even more preferably 100 parts by mass or less, with respect to 100 parts by mass of the amount of the first solvent.

In addition, after the second solvent is charged, a part of the first solvent and second solvent may be removed to precipitate the compound (4). As the method of removing a part of the first solvent and second solvent, concentration under reduced pressure is preferable. When performing the concentration under reduced pressure, the reaction liquid may be heated. The temperature of the reaction liquid when performing the concentration is preferably 100° C. or less, more preferably 80° C. or less, and even more preferably 60° C. or less.

Examples of the method of removing the precipitate include a method of filtering the reaction liquid. The target first complex is obtained by removing the first solvent and the second solvent from the filtrate from which the precipitate has been removed.

(Purification Step)

In the purification step, the mixture containing the first complex and the compound (4), which is obtained in the recovery step and/or the precipitation step, is reprecipitated. Specifically, after the obtained mixture containing the first complex and the compound (4) is dissolved in the first solvent, the second solvent is charged into the first solvent in which the mixture containing the first complex and the compound (4) is dissolved to precipitate the compound (4), and the precipitate is removed.

Examples of the first solvent and the second solvent used in the purification step include those listed in the reaction step and the precipitation step. In addition, the preferable amount of the second solvent and the preferable method of removing the precipitate are same as those in the above precipitation step. The target first complex is obtained by removing the precipitate and then removing the solvent from the resultant filtrate. The preferable method of removing the solvent is same as that in the recovery step. It is noted that the purification step may be performed several times depending on the desired purity of the first complex.

The second preparing process according to the present invention comprises a step of reacting the obtained first complex with water to obtain the second complex (second reaction step). In the second reaction step, examples of the method of reacting the first complex with water include a method of exposing the first complex under a high humidity atmosphere. The humidity of the high humidity atmosphere is preferably 50% RH or more, more preferably 60% RH or more, and even more preferably 70% RH or more. In addition, the temperature of the high humidity atmosphere (atmospheric temperature) is preferably 0° C. or more, more preferably 10° C. or more, and even more preferably 20° C. or more, and is preferably 200° C. or less, more preferably 150° C. or less, and even more preferably 100° C. or less.

The amount of water with respect to the first complex is not particularly limited, and is preferably 3 parts by mass or more, more preferably 5 parts by mass or more, and even more preferably 10 parts by mass or more, with respect to 100 parts by mass of the first complex. If the amount of water is 3 parts by mass or more, the reaction efficiency of the first complex with water is enhanced. The upper limit of the amount of water is not particularly limited, and is preferably 100 parts by mass, more preferably 50 parts by mass, with respect to 100 parts by mass of the first complex.

The reaction product of the first complex and water is preferably purified. This is because the purity of the second complex is increased.

The present invention further includes a process of preparing a complex comprising a step of reacting a carboxylic acid represented by a formula (6) with a metal oxide represented by a formula (5) in a solvent (third preparing process):

(6)

(5)

[In the formula (6), R is a hydrogen atom, an alkyl group having 1 to 18 carbon atoms, an alkenyl group having 2 to 18 carbon atoms or an alkynyl group having 2 to 18 carbon atoms. In the formula (5), $M^7$ is a metal atom, a is an integer of 1 to 5, and b is an integer of 1 to 7.].

In the third preparing process, water is generated by the reaction of the carboxylic acid (6) with the metal oxide (5). Thus, water is not necessarily added into the reaction system, unlike the first preparing process and the second preparing process.

R in the carboxylic acid (6) is a hydrogen atom, an alkyl group having 1 to 18 carbon atoms, an alkenyl group having 2 to 18 carbon atoms or an alkynyl group having 2 to 18 carbon atoms.

Examples of the alkyl group having 1 to 18 carbon atoms include methyl group, ethyl group, propyl group, butyl group, pentyl group, hexyl group, heptyl group, octyl group, nonyl group, decyl group, undecyl group, dodecylgroup, tridecyl group, tetradecyl group, pentadecyl group, hexadecyl group, heptadecyl group, and octadecyl group. The alkyl group having 1 to 18 carbon atoms may have a linear structure, a branched structure or a cyclic structure, and the linear structure is preferable.

Examples of the alkenyl group having 2 to 18 carbon atoms include ethenyl group (vinyl group), 1-propenyl group, 2-propenyl group, isopropenyl group, butenyl group, pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, and octadecenyl group. The alkenyl group having 2 to 18 carbon atoms may have a linear structure or a branched structure, and the linear structure is preferable. As the alkenyl group having 2 to 18 carbon atoms, an alkenyl group having one carbon-carbon double bond is preferable. The position of the carbon-carbon double bond is preferably α, β-position or a terminal of the alkenyl group. The alkenyl group preferably has 8 or less carbon atoms, more preferably 6 or less carbon atoms, and even more preferably 4 or less carbon atoms. Preferable examples of the alkenyl group having 2 to 18 carbon atoms include vinyl group, isopropenyl group, 1-propenyl group and 2-propenyl group.

Examples of the alkynyl group having 2 to 18 carbon atoms include ethynyl group, 1-propynyl group, 2-propynyl group, isopropynyl group, butynyl group, pentynyl group, hexynyl group, heptynyl group, octynyl group, nonynyl group, decynyl group, undecynyl group, dodecynyl group, tridecynyl group, tetradecynyl group, pentadecynyl group, hexadecynyl group, heptadecynyl group, and octadecynyl group. The alkynyl group having 2 to 18 carbon atoms may have a linear structure or a branched structure, and the linear structure is preferable. As the alkynyl group having 2 to 18 carbon atoms, an alkynyl group having one carbon-carbon triple bond is preferable. The position of the carbon-carbon triple bond is preferably α, β-position or a terminal of the alkynyl group. The alkynyl group preferably has 8 or less carbon atoms, more preferably has 6 or less carbon atoms, and even more preferably has 4 or less carbon atoms. Preferable examples of the alkynyl group having 2 to 18 carbon atoms include ethynyl group, isopropynyl group, 1-propynyl group and 2-propynyl group.

Specific examples of the carboxylic acid (6) include a saturated fatty acid having 1 to 19 carbon atoms, and an unsaturated fatty acid having 3 to 20 carbon atoms.

Examples of the saturated fatty acid include methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, and nonadecanoic acid. Examples of the unsaturated fatty acid include an unsaturated fatty acid having a carbon-carbon double bond such as propenoic acid (acrylic acid), 2-methylprop-2-enoic acid (methacrylic acid), 2-butenoic acid, 3-butenoic acid, 4-pentenoic acid, 5-hexenoic acid, 6-heptenoic acid, 7-octenoic acid, 8-nonenoic acid, 9-decenoic acid, 10-undecenoic acid, 11-dodecenoic acid, 12-tridecenoic acid, 9-tetradecenoic acid, 13-tetradecenoic acid, 14-pentadecenoic acid, 9-hexadecenoic acid, 15-hexadecenoic acid, 16-heptadecenoic acid, 9-octadecenoic acid, 11-octadecenoic acid, 17-octadecenoic acid and 18-nonadecenoic acid; and an unsaturated fatty acid having a carbon-carbon triple bond such as propiolic acid, 3-butynoic acid, 4-pentynoic acid, 5-hexynoic acid, 6-heptynoic acid, 7-octynoic acid, 8-nonynoic acid, 9-decynoic acid, 10-undecynoic acid, 11-dodecynoic acid, 12-tridecynoic acid, 9-tetradecynoic acid, 13-tetradecynoic acid, 14-pentadecynoic acid, 9-hexadecynoic acid, 15-hexadecynoic acid, 16-heptadecynoic acid, 9-octadecynoic acid, 11-octadecynoic acid, 17-octadecynoic acid and 18-nonadecynoic acid.

As the unsaturated fatty acid having a carbon-carbon double bond, a fatty acid having one carbon-carbon double bond is preferable. The position of the carbon-carbon double bond is preferably α, β-position or a terminal of the unsaturated fatty acid. As the unsaturated fatty acid having a carbon-carbon triple bond, a fatty acid having one carbon-carbon triple bond is preferable. The position of the carbon-carbon triple bond is preferable α, β-position or a terminal of the unsaturated fatty acid.

When two or more of the fatty acids are used in combination as the carboxylic acid (6), the amount of each fatty acid can be suitably adjusted in accordance with the desired complex. The amount of the unsaturated fatty acid in the fatty acid constituting the carboxylic acid (6) is preferably 33 mol % or more, more preferably 50 mol % or more, and even more preferably 66 mol % or more. It is also preferable that all the fatty acids constituting the carboxylic acid (6) are the unsaturated fatty acid. In addition, the amount of the unsaturated fatty acid having a carbon-carbon double bond in the fatty acid constituting the carboxylic acid (6) is preferably 33 mol % or more, more preferably 50 mol % or more, and even more preferably 66 mol % or more. It is also preferable that all the fatty acids constituting the carboxylic acid (6) are the unsaturated fatty acid having a carbon-carbon double bond. As the fatty acid constituting the carboxylic acid (6), a plurality of fatty acids may be used in combination, but one fatty acid is preferably used.

The carboxylic acid (6) is preferably acrylic acid and/or methacrylic acid.

The metal oxide represented by the formula (5) will be explained.

$$M^7_a O_b \qquad (5)$$

Examples of the metal atom ($M^7$) include an alkali metal such as lithium, sodium, potassium, rubidium and cesium; an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; and a base metal such as beryllium, magnesium, aluminum, zinc, gallium, cadmium, indium, tin, thallium, lead, bismuth and polonium. Among them, the metal atom $M^7$ is preferably a metal atom capable of forming a divalent metal ion, and more preferably beryllium, magnesium, calcium, zinc, barium, cadmium or lead. These metal atoms may be used solely, or at least two of them may be used in combination.

In the metal oxide (5), a is preferably an integer of 1 or more and 5 or less, more preferably an integer of 1 or more and 3 or less, and most preferably 1, and b is preferably an integer of 1 or more and 7 or less, more preferably an integer of 1 or more and 5 or less, even more preferably an integer of 1 or more and 3 or less, and most preferably 1. As the metal oxide (5), a divalent metal oxide with a=1 and b=1 is preferable.

Specific examples of the metal oxide (5) include an alkali metal oxide such as lithium oxide, sodium oxide, potassium oxide, rubidium oxide and cesium oxide; an alkaline earth metal oxide such as calcium oxide, strontium oxide and barium oxide; a transition metal oxide such as scandium oxide, titanium oxide, vanadium oxide, chromium oxide, manganese oxide, iron oxide, cobalt oxide, nickel oxide, copper oxide, yttrium oxide, zirconium oxide, niobium oxide, molybdenum oxide, technetium oxide, ruthenium oxide, rhodium oxide, palladium oxide, silver oxide, hafnium oxide, tantalum oxide, tungsten oxide, rhenium oxide, osmium oxide, iridium oxide, platinum oxide and gold oxide; and a base metal oxide such as beryllium oxide, magnesium oxide, aluminum oxide, zinc oxide, gallium oxide, cadmium oxide, indium oxide, tin oxide, thallium oxide, lead oxide, bismuth oxide and polonium oxide. These metal oxides may be used solely, or a mixture of at least two of them may be used. Among them, as the metal oxide, the divalent metal oxide is preferable, and beryllium oxide, magnesium oxide, calcium oxide, zinc oxide, barium oxide, cadmium oxide or lead oxide is more preferable. In the present invention, as the metal oxide (5), zinc oxide is most preferably used.

Examples of the first solvent used in the reaction step of the third preparing process include, but are not limited to, dichloromethane, 1,2-dichloroethane, chloroform, chlorobenzene, dichlorobenzene, benzene, toluene, xylene, tetrahydrofuran, 1,4-dioxane, ethyl acetate, propyl acetate, isopropyl acetate, acetonitrile, methanol, ethanol, propanol, and isopropanol. From the viewpoint of enhancing the yield of the complex, dichloromethane is preferably used as the solvent.

Specifically, the process of preparing a complex comprising the step of reacting the carboxylic acid (6) with the metal oxide (5) preferably comprises, for example, a step of dissolving or dispersing the carboxylic acid (6) and the metal oxide (5) in a first solvent and stirring the resultant reaction liquid (reaction step); a step of removing an insoluble substance from the reaction liquid (insoluble substance removal step); and a step of precipitating the target complex from the reaction liquid (precipitation step).

(Reaction Step)

In the reaction step, the carboxylic acid (6) and the metal oxide (5) are dissolved or dispersed in the first solvent, and the resultant reaction liquid is stirred. In this step, the carboxylic acid (6) and the metal oxide (5) are allowed to contact each other in the solvent to produce the complex.

Specifically, in a reaction vessel, the metal oxide (5) is firstly dissolved or dispersed in a solvent. While stirring the liquid obtained by dissolving or dispersing the metal oxide (5) in the solvent, a liquid obtained by dissolving or dispersing the carboxylic acid (6) in a solvent is added dropwise therein. The dropwise addition time of the liquid obtained by dissolving or dispersing the carboxylic acid (6) in the solvent is preferably, but not limited to, 0.5 hour to 3 hours. The reaction is preferably carried out while further stirring the reaction liquid after the dropwise addition.

The reaction is preferably carried out in an inert gas atmosphere such as argon and nitrogen.

In the reaction of the carboxylic acid (6) with the metal oxide (5), the molar ratio ((6)/(5)) of the carboxylic acid (6) to the metal oxide (5) is preferably more than 1/2, more preferably 1/1 or more, and is preferably 2/1 or less, more preferably 7/4 or less. This is because if the molar ratio ((6)/(5)) of the carboxylic acid (6) to the metal oxide (5) falls within the above range, the yield of the obtained complex is higher.

In addition, the amount of the first solvent used in the reaction step is preferably 1000 parts by mass or more, more preferably 2000 parts by mass or more, and even more preferably 3000 parts by mass or more, and is preferably 10000 parts by mass or less, more preferably 8000 parts by mass or less, and even more preferably 6000 parts by mass or less, with respect to 100 parts by mass of a total amount of the carboxylic acid (6) and the metal oxide (5). If the amount of the first solvent exceeds 10000 parts by mass, the synthetic workload increases, and if the amount of the first solvent is less than 1000 parts by mass, the yield of the complex may be lowered.

The reaction temperature (temperature of the reaction liquid) in the reaction step is preferably −20° C. or more, more preferably 0° C. or more, even more preferably 10° C. or more, and most preferably 20° C. or more, and is preferably 100° C. or less, more preferably 90° C. or less, even more preferably 80° C. or less, and most preferably 50° C. or less. If the reaction temperature is −20° C. or more, the reaction speed between the carboxylic acid (6) and the metal oxide (5) can be enhanced. In addition, if the reaction temperature is 100° C. or less, the self-polymerization of the carboxylic acid (6) can be prevented.

The reaction time in the reaction step is preferably 1 hour or more, more preferably 2 hours or more, and even more preferably 3 hours or more. This is because if the reaction time is too short, the yield of the complex may be lowered. In addition, from the viewpoint of enhancing the productivity, the reaction time is preferably 300 hours or less, more preferably 200 hours or less, and even more preferably 100 hours or less. It is noted that the end of the reaction can be confirmed, for example, by a method of measuring the infrared absorption of a sample taken from the reaction liquid, or by a method of measuring the change in the weight or the like of the component dissolved in the reaction liquid.

The third preparing process according to the present invention preferably comprises an insoluble substance removal step, a precipitation step, a recovery step or a purification step, after the reaction of the carboxylic acid (6) with the metal oxide (5) is ended.

(Insoluble Substance Removal Step)

After the reaction is ended, the insoluble substance is removed from the reaction liquid. Examples of the insoluble substance include unreacted raw materials, and the self-polymerized polymer of the carboxylic acid (6). Examples of the method of removing the insoluble substance include, but are not limited to, a method of filtering the reaction liquid.

(Precipitation Step)

In the precipitation step, a second solvent is charged into the reaction liquid from which the insoluble substance has been removed to precipitate the target complex dissolved in the first solvent. The reaction liquid contains, for example, the target complex and the unreacted carboxylic acid (6). If the solubility of the target complex in the second solvent is lower than the solubility of the carboxylic acid (6) in the second solvent, the target complex can be selectively precipitated. The second solvent is not particularly limited, as long as it can selectively precipitate the target complex in the reaction liquid. Examples of the second solvent include hydrocarbons such as hexane, pentane, cyclohexane and heptane.

The amount of the second solvent may be suitably adjusted such that the target complex can be precipitated. The amount of the second solvent is preferably 10 parts by mass or more, more preferably 20 parts by mass or more, and even more preferably 30 parts by mass or more, and is preferably 200 parts by mass or less, more preferably 150 parts by mass or less, and even more preferably 100 parts by mass or less, with respect to 100 parts by mass of the amount of the first solvent.

In addition, after the second solvent is charged, a part of the first solvent and second solvent may be removed to precipitate the target complex. As the method of removing a part of the first solvent and second solvent, concentration under reduced pressure is preferable. When performing the concentration under reduced pressure, the reaction liquid may be heated. The temperature of the reaction liquid when performing the concentration is preferably 100° C. or less, more preferably 80° C. or less, and even more preferably 60° C. or less.

The precipitated target complex is preferably filtered and dried.

(Recovery Step)

In the recovery step, the solvent is removed from the reaction liquid from which the insoluble substance has been removed. The target complex existing in the reaction liquid can be recovered by removing the solvent.

Examples of the method of removing the solvent include a method of drying under reduced pressure and a method of drying under heating, and the drying under reduced pressure is preferable. When performing the drying under reduced pressure, the reaction liquid may be heated. The temperature of the reaction liquid when performing the drying is preferably 100° C. or less, more preferably 80° C. or less, and even more preferably 60° C. or less.

(Purification Step)

In the purification step, the purity of the target complex can be increased by reprecipitating the target complex obtained in the precipitation step or the recovery step. Specifically, after the obtained target complex is dissolved in the first solvent, the second solvent is charged into the first solvent in which the target complex is dissolved to precipitate the target complex, and the target complex is recovered.

Examples of the first solvent and the second solvent used in the purification step include those listed in the above reaction step and precipitation step. In addition, the preferable amount of the second solvent is also same as that in the above precipitation step. The purification step may be performed several times depending on the desired purity of the target complex.

The process of preparing a complex according to the present invention is suitable as a method of preparing the complex represented by the formula (1) and the complex represented by the structural formula (2) or (3). Details of the complex represented by the formula (1) are described as above, and its gist is as follows.

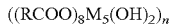
$$((RCOO)_8M_5(OH)_2)_n \quad (1)$$

[In the formula (1), M is a metal atom, and R is a hydrogen atom, an alkyl group having 1 to 18 carbon atoms, an alkenyl group having 2 to 18 carbon atoms or an alkynyl group having 2 to 18 carbon atoms. A plurality of R may be identical to or different from each other, and at least one of R is the alkenyl group having 2 to 18 carbon atoms or the alkynyl group having 2 to 18 carbon atoms. n is an integer of 1 or more.].

Details of the complex represented by the structural formula (2) are described as above, and its gist is as follows.

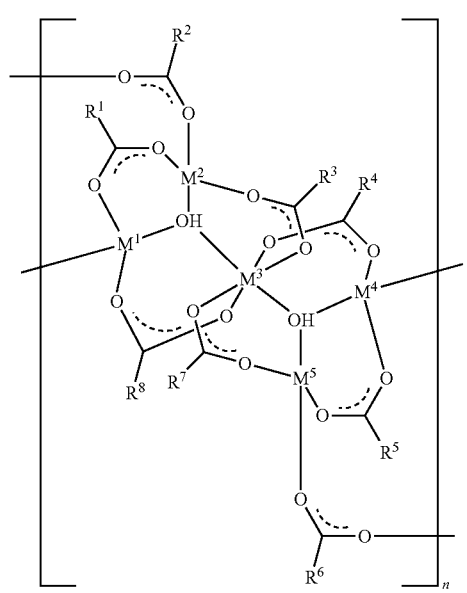

(2)

[In the formula (2), $M^1$ to $M^5$ are identical to or different from each other and represent a metal atom, O represents an oxygen atom, H represents a hydrogen atom, $R^1$ to $R^8$ are identical to or different from each other and represent a hydrogen atom, an alkyl group having 1 to 18 carbon atoms, an alkenyl group having 2 to 18 carbon atoms or an alkynyl group having 2 to 18 carbon atoms, n is an integer of 1 or more, and at least one of $R^1$ to $R^8$ is the alkenyl group having 2 to 18 carbon atoms or the alkynyl group having 2 to 18 carbon atoms.].

Details of the complex represented by the structural formula (3) are described as above, and its gist is as follows.

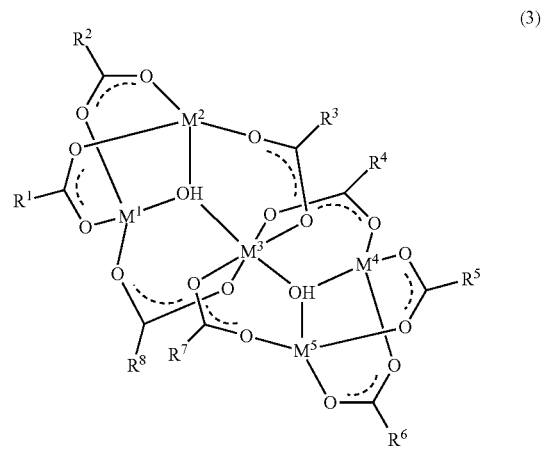

(3)

[In the formula (3), $M^1$ to $M^5$ are identical to or different from each other and represent a metal atom, O represents an oxygen atom, H represents a hydrogen atom, $R^1$ to $R^8$ are identical to or different from each other and represent a hydrogen atom, an alkyl group having 1 to 18 carbon atoms, an alkenyl group having 2 to 18 carbon atoms or an alkynyl group having 2 to 18 carbon atoms, and at least one of $R^1$ to $R^8$ is the alkenyl group having 2 to 18 carbon atoms or the alkynyl group having 2 to 18 carbon atoms.]

EXAMPLES

Next, the present invention will be described in detail by way of examples. However, the present invention is not limited to the examples described below. Various changes and modifications without departing from the spirit of the present invention are included in the scope of the present invention.

[Evaluation Methods]

(1) Direct Introduction-Mass Analysis (DI-MS)

The mass analysis was carried out with a mass analyzer (SynaptG2-S type available from Waters Corporation).

Ionization method: atmospheric solids analysis probe (ASAP)

Measuring mode: Pos., Neg.

Measuring range: m/z=50 to 1500

(2) CHN Element Analysis

The element analysis was carried out with an organic trace element analyzer (Micro Corder JM10 type available from J-Science Lab Co., Ltd.).

(3) Zinc Amount Measurement

The complex (0.1057 g) was weighed and put into a beaker with a volume of 100 ml, and 50 ml of distilled water was added to dissolve the complex. Into the resultant liquid, 10 ml of acetic acid-sodium acetate (pH 5) buffer was added, and some drops of a XO indicator (0.1 w/v % of xylenol orange solution for titration available from Wako Pure Chemical Industries, Ltd.: 0.1 g/100 ml=0.001396 M) were added. Finally, distilled water was added to adjust the liquid volume to 100 ml. The obtained liquid was titrated with 0.05 mol/l of an EDTA standard titrant (available from Dojin Chemical, Inc.).

(4) Infrared Spectroscopic Analysis

The infrared spectroscopic analysis was carried out with a Fourier transform infrared spectrophotometer ("measuring instrument: Spectrum One" available from PerkinElmer, Inc.) by a total reflection absorption measuring method (ATR method) using diamond as a prism of the total reflection absorption measurement.

(5) Powder X-ray Diffraction

The X-ray diffraction measurement was carried out with a wide angle X-ray diffraction instrument ("RINT-TTR III type" available from Rigaku Corporation). The measuring sample was pulverized with an agate mortar. The measuring conditions were as follows.

X-ray source: CuKα X-ray
Tube voltage-tube current: 50 kV-300 mA
Step width: 0.02 deg.
Measuring speed: 5 deg./min
Slit system: light diffusion-light reception-light scattering: 0.5 deg.-opening-0.5 deg.
Monochromator: diffraction curve bent-crystal monochromator (6) Single Crystal X-ray Diffraction Structure Analysis (X-ray Diffraction Analysis)

Device: XtaLAB PRO MM007
Data processing Software: CrysAlisPro
Structure analysis program package: CrystalStructure
X-ray source: Cu Kα (λ=1.54184 angstrom)
Tube voltage, tube current: 40 kV-30 mA
Measurement temperature: −173° C. (Use of Low temperature device)
Collimator diameter: φ 0.5 mm
Camera length: 39.25 mm
Oscillation angle: 0.20°

A measurement sample was produced as follows.

The complex (5 mg) and ethyl acetate (833 μL) were charged into the 4 mL of vial and heated to the temperature of 60° C. to dissolve the complex (concentration 6 mmg/mL). The solution was left for a month at the temperature of 20° to give a single crystal having a hexagonal shape of 0.1 mm of the complex. The crystal was taken from the vial and put into the Paratone-N (Hampton Research) on the hole slide glass. The crystal and Paratone-N were dipped together with MicroLoop LD100·mφ (MiTeGen), and rapidly frozen with a gas stream provided by a low temperature device to measure X-ray diffraction. Data measurement and processing for X-ray diffraction was conducted by a software of CrysAlisPro and Structure analysis program package of Crystal Structure.

Preparing Examples

Inventive Preparing Example 1

Zinc oxide (10 g, 123 mmol) and 250 ml of dichloromethane were charged into a reaction vessel, and stirred at 0° C. in an ice bath. A liquid obtained by dissolving acrylic acid (12.6 g, 174 mmol) in 125 ml of dichloromethane was added dropwise therein at a dropwise addition speed of 2 ml/min. After the dropwise addition, the ice bath was taken away, and stirring was performed at room temperature (rt) for 12 hours. The obtained reaction liquid was filtered to remove the insoluble precipitate in the solvent. 300 ml of hexane was added into the filtrate, and concentration under reduced pressure was performed until the liquid amount was reduced to about one-fourth, to obtain a precipitate. The precipitate was taken out by filtration, and dried to obtain a complex 1 (output: 7.18 g, yield: 35%). It is noted that the following materials were used in the inventive preparing example 1.

Zinc oxide: available from Kishida Chemical Co. Ltd.
Acrylic acid: available from Sigma-Aldrichi Corporation
Dichloromethane: available from Kishida Chemical Co. Ltd.
Hexane: available from Kishida Chemical Co. Ltd.

The infrared spectroscopic analysis, element analysis, zinc amount measurement and X-ray diffraction measurement were conducted for the complex 1 obtained in the inventive preparing example 1. The experimental results are each shown below.

IR spectrum peak: 413 cm$^{-1}$, 469 cm$^{-1}$, 688 cm$^{-1}$, 829 cm$^{-1}$, 972 cm$^{-1}$, 1068 cm$^{-1}$, 1274 cm$^{-1}$, 1372 cm$^{-1}$, 1435 cm$^{-1}$, 1522 cm$^{-1}$, 1568 cm$^{-1}$, 1644 cm$^{-1}$.

Anal. Calcd for $C_{24}H_{26}O_{18}Zn_5$: C, 31.02; H, 2.82. Found: C, 30.36; H, 2.77.

Figure 2:
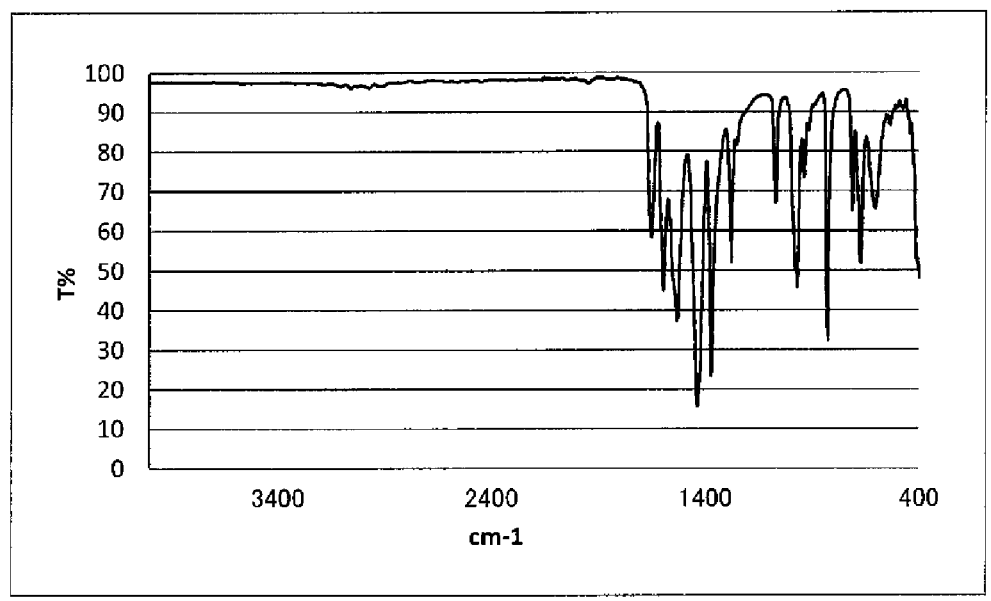
FIG. 2 shows IR spectrum of zinc diacrylate.

FIG. 1 shows IR spectrum of the complex 1 obtained in the inventive preparing example 1, and FIG. 2 shows IR spectrum of zinc diacrylate. Based on the IR spectra, the absorption attributed to the vinyl group of acrylate and the absorption attributed to the vibration of (HO)Zn$_3$ are confirmed. Further, two types of absorption attributed to the vibration of the carboxylate groups which have different coordination states from each other are confirmed.

The amount of zinc was measured as follows. The complex 1 obtained in the inventive example 1 (0.1057 g) was weighed in a 100 ml of beaker, and 50 ml of distilled water was added into the beaker to dissolve the complex 1. The 10 ml of acetic acid-sodium acetate buffer solution (pH5) was added into this solution, and some drops of a XO indicator (0.1 w/v % xyleynol orange solution for titration available form Wako Pure Chemical Industries, Ltd.: 0.1 g/100 ml=0.001396M) were added. The obtained liquid was titrated with 0.05 mol/l of an EDTA standard titrant (available from Dojin Chemical, Inc.). Titration was ended when the color changed from red-violet to yellow, and the zinc amount was determined with the titration amount of 11.53 ml at the titration end point. The measured value of the zinc amount is 35.7 mass %, which is very close to the theoretical value of 35.2 mass %. These results indicate that the complex 1 produced above is a compound represented by $Zn_5(OCOCHCH_2)_8(OH)_2$.

The element analysis results show that the complex 1 obtained in the inventive preparing example 1 contains carbon in an amount of 30.36 mass % and hydrogen in an amount of 2.77 mass %. The differences between the analysis results and the estimated values were 0.66 mass % for the carbon amount and 0.05 mass % for the hydrogen amount. Since the atomic composition is very close to the estimated value, it can be confirmed that the complex 1 ($Zn_5(OCOCHCH_2)_8(OH)_2$) has a very high purity.

Figure 3:
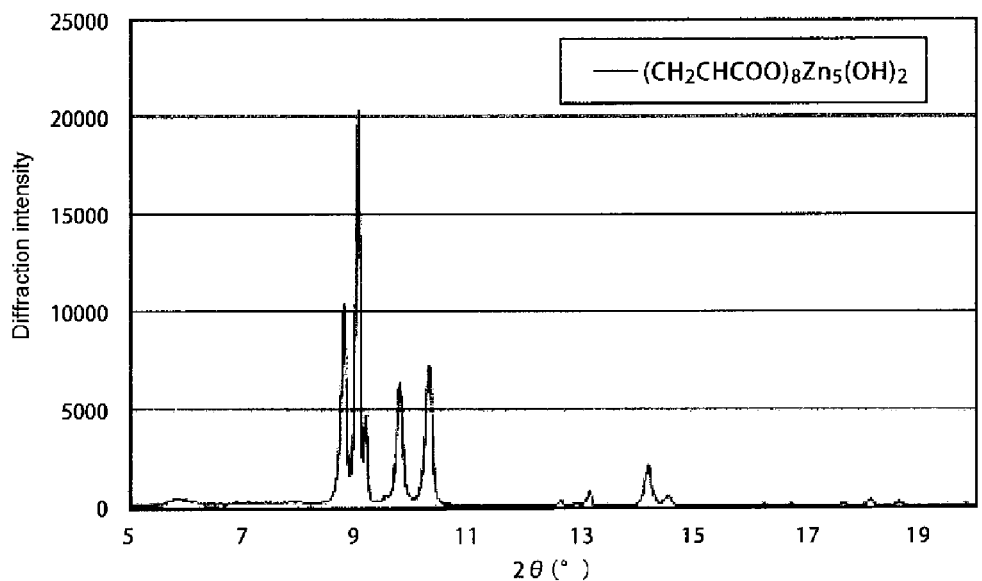
FIG. 3 shows X-ray diffraction spectrum of a preferable complex according to the present invention.
Figure 4:
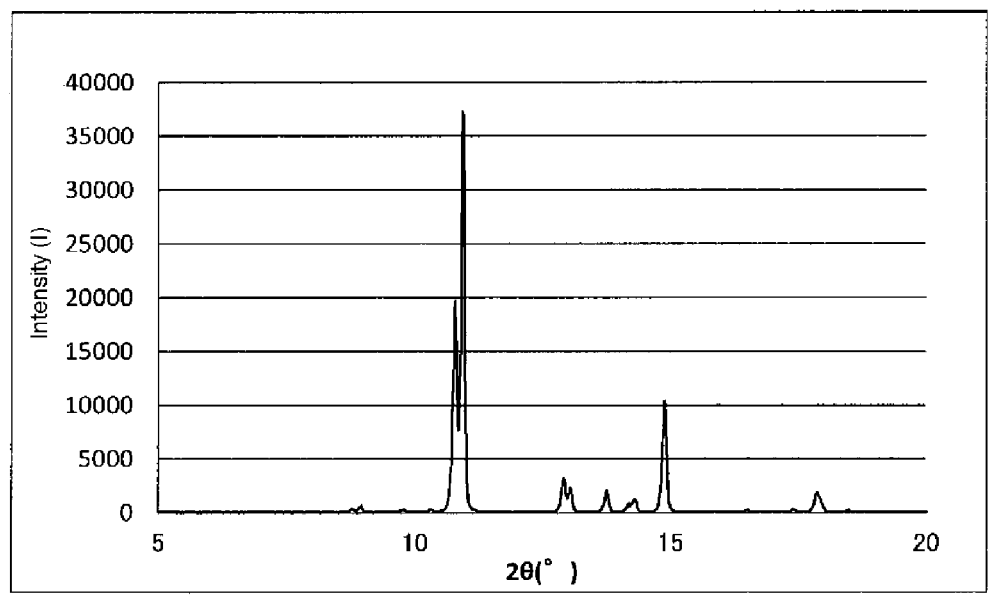
FIG. 4 shows X-ray diffraction spectrum of zinc diacrylate.

FIG. 3 shows X-ray diffraction spectrum of the complex 1 obtained in the inventive preparing example 1, and FIG. 4 shows X-ray diffraction spectrum of zinc diacrylate. Based on the X-ray diffraction spectra, it is confirmed that the complex 1 obtained in the inventive preparing example 1 has a different crystal structure from zinc diacrylate.

Inventive Preparing Example 2

Zinc oxide (2.5 g, 31 mmol), zinc acrylate (19.1 g, 92 mmol), 375 ml of dichloromethane and water (0.75 ml, 41 mmol) were charged into a reaction vessel, and stirred at 40° C. for 3 hours. It is noted that the solvent was refluxed. The obtained reaction liquid was filtered to remove the insoluble precipitate in the solvent. 300 ml of hexane was added into the filtrate, and concentration under reduced pressure was performed until the liquid amount was reduced to about one-fourth, to obtain a precipitate. The precipitate was taken out by filtration, and dried to obtain a complex 2 (6.72 g, yield 31%).

Figure 5:
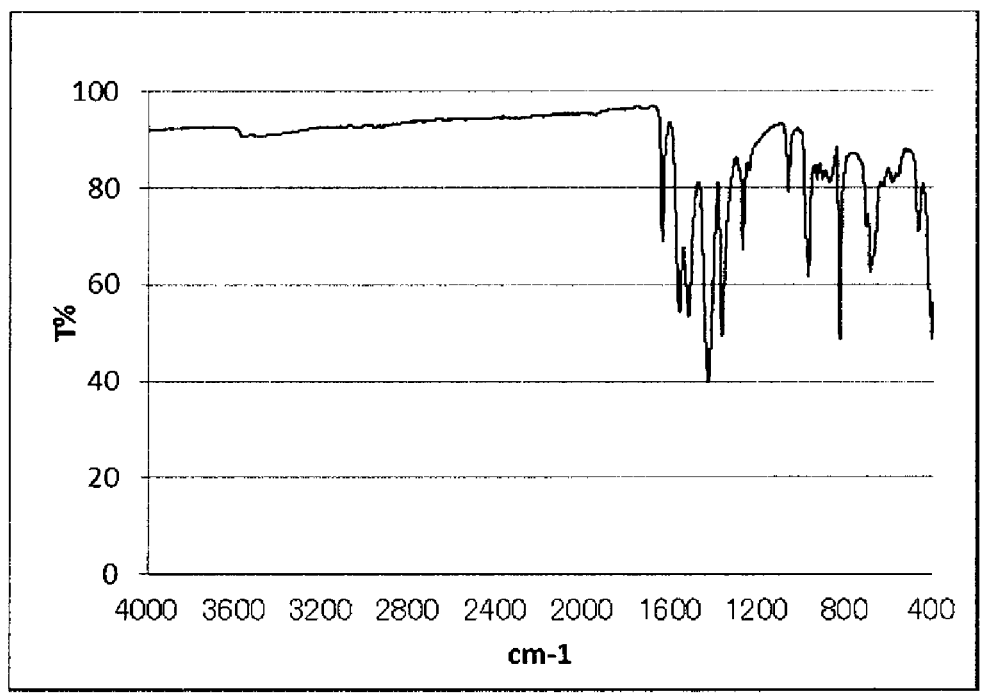
FIG. 5 shows IR spectrum of a preferable complex according to the present invention.

FIG. 5 shows IR spectrum of the complex 2 obtained in the inventive preparing example 2.

IR spectrum peak: 405 $cm^{-1}$, 469 $cm^{-1}$, 688 $cm^{-1}$, 829 $cm^{-1}$, 972 $cm^{-1}$, 1066 $cm^{-1}$, 1273 $cm^{-1}$, 1366 $cm^{-1}$, 1431 $cm^{-1}$, 1522 $cm^{-1}$, 1564 $cm^{-1}$, 1642 $cm^{-1}$.

Based on the IR spectrum of the complex 2 obtained in the inventive preparing example 2, the absorption attributed to the vinyl group of acrylate and the absorption attributed to the vibration of $(HO)Zn_3$ are confirmed. Further, two types of absorption attributed to the vibration of the carboxylate groups which have different coordination states from each other are confirmed.

The preparing conditions and results of the inventive preparing examples 1 to 2 are summarized in Table 1.

and dried to obtain the first complex 3. The obtained first complex 3 was allowed to slowly react with water (moisture) under an atmosphere of 20° C. to 30° C. and humidity of 50% or more to obtain the second complex 3 (target complex, 116 g, yield 12%).

Inventive Preparing Example 4

The reaction was carried out by the same method as the inventive preparing example 3 except that the reaction was continued for 12 hours after the temperature of the reaction liquid reached to 40° C., and then finished to obtain the second complex 4 (target complex, output: 79 g, yield: 8%).

Inventive Preparing Example 5

The reaction was carried out by the same method as the inventive preparing example 3 except that the reaction was continued for 24 hours after the temperature of the reaction liquid reached to 40° C., and then finished to obtain the second complex 5 (target complex, output: 25 g, yield: 3%).

TABLE 1

| Inventive preparing example | Compounds (4) or (6) (g) | (mmol) | Metal oxide (5) (g) | (mmol) | Compounds (4), (6)/metal oxide (5) (molar ratio) | Solvent (ml) | Temperature (° C.) | Time (h) | Water (ml) | Output (g) | Yield (%) |
|---|---|---|---|---|---|---|---|---|---|---|---|
| 1 | AA 12.6 | 174 | ZnO 10 | 123 | 2.8:2 | Dichloromethane 250 + 125 ml | 0° C. to rt | 12 | None | 7.18 | 35 |
| 2 | ZDA 19 | 92 | ZnO 2.5 | 31 | 3:1 | Dichloromethane 375 ml | 40° C. | 3 | 0.75 | 6.72 | 31 | rt: room temperature,
AA: acrylic acid,
ZDA: zinc acrylate
Yield (%) = 100 × (value obtained by dividing each output by molecular weight of cluster)/(theoretical value (mole) of cluster estimated from raw materials)

Inventive Preparing Example 3

Under an argon atmosphere, zinc oxide (125 g, 1540 mmol), zinc acrylate (955 g, 4600 mmol) and 18.7 L of dichloromethane were charged into a reaction vessel, and stirred at 40° C. for 3 hours. It is noted that the solvent was refluxed. The obtained reaction liquid was filtered to remove the insoluble precipitate in the solvent. 14.3 L of hexane was added into the filtrate, and concentration under reduced pressure was performed until the liquid amount was reduced to about one-fourth, to obtain a precipitate. The precipitate was taken out by filtration, and the filtrate was concentrated Inventive Preparing Example 6

The reaction was carried out by the same method as the inventive preparing example 3 except that the reaction was continued for 48 hours after the temperature of the reaction liquid reached to 40° C., and then finished to obtain the second complex 6 (target complex, output: 70 g, yield: 8%).

The preparing conditions and results of the inventive preparing examples 3 to 6 are summarized in Table 2.

TABLE 2

| Inventive preparing example | Compound (4) (g) | (mmol) | Metal oxide (5) (g) | (mmol) | Compound (4)/metal oxide (5) (molar ratio) | Solvent (ml) | Temperature (° C.) | Time (h) | Output (g) | Yield (%) |
|---|---|---|---|---|---|---|---|---|---|---|
| 3 | ZDA 955 | 4600 | ZnO 125 | 1540 | 3:1 | Dichloromethane 18700 | 40° C. | 3 | 116 | 12 |
| 4 | ZDA 955 | 4600 | ZnO 125 | 1540 | 3:1 | Dichloromethane 18700 | 40° C. | 12 | 79 | 8 |
| 5 | ZDA 955 | 4600 | ZnO 125 | 1540 | 3:1 | Dichloromethane 18700 | 40° C. | 24 | 25 | 3 |
| 6 | ZDA 955 | 4600 | ZnO 125 | 1540 | 3:1 | Dichloromethane 18700 | 40° C. | 48 | 70 | 8 |

ZDA: zinc acrylate
Yield (%) = 100 × (value obtained by dividing each output by molecular weight of cluster)/(theoretical value (mole) of cluster estimated from raw materials)

The mass analysis, element analysis, zinc amount measurement, X-ray diffraction measurement and infrared spectroscopic analysis were conducted for the first complex 3 obtained in the inventive preparing example 3. The experimental results are each shown below.

High-resolution ASAP-MS (positive) spectrum measurement results

Positive ion HR-ASAP-MS m/z: 632.7715
$[M-CH_2CHCOO]^+$ (calcd. For $C_{15}H_{15}O_{11}Zn_4$ 632.7707 $\Delta 1.2$ ppm High-resolution ASAP-MS (negative) spectrum measurement results Negative ion HR-ASAP-MS m/z: 735.7762
$[M+O_2]^-$ (calcd. For $C_{18}H_{18}O_{15}Zn_4$ 735.7740 $\Delta 2.9$ ppm
Anal. Calcd for $C_{18}H_{18}O_{13}Zn_4$: C, 30.71; H, 2.58. Found: C, 30.72; H, 2.50.

IR spectrum peak: 520 $cm^{-1}$, 600 $cm^{-1}$, 675 $cm^{-1}$, 828 $cm^{-1}$, 968 $cm^{-1}$, 1067 $cm^{-1}$, 1276 $cm^{-1}$, 1370 $cm^{-1}$, 1436 $cm^{-1}$, 1572 $cm^{-1}$, 1643 $cm^{-1}$.

Figure 6:
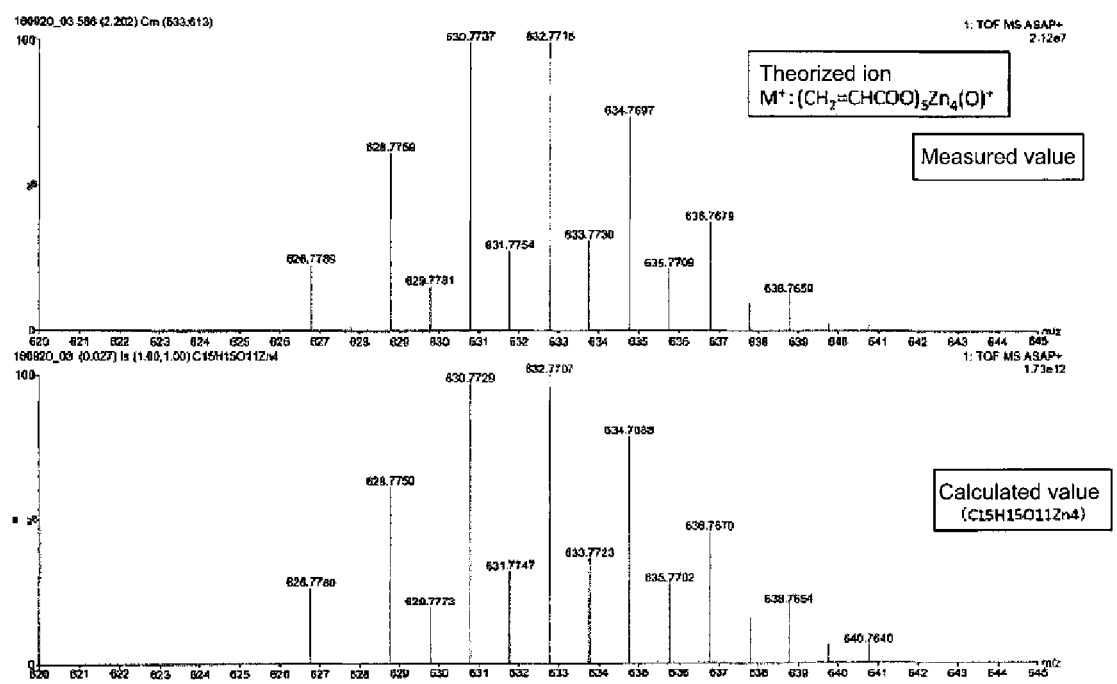
FIG. 6 shows ASAP-MS spectrum of an intermediate complex obtained in the preparing process according to the present invention.
Figure 7:
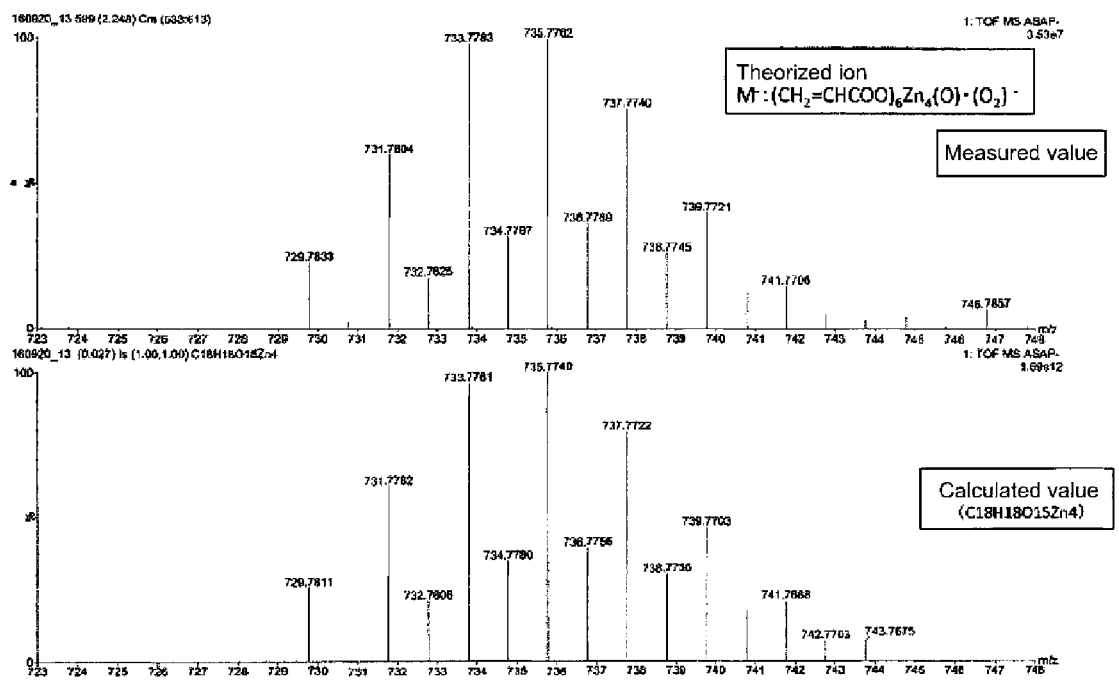
FIG. 7 shows ASAP-MS spectrum of an intermediate complex obtained in the preparing process according to the present invention.

ASAP-MS spectra of the first complex 3 obtained in the inventive preparing example 3 are shown in FIGS. 6, 7. In addition, ASAP-MS spectrum simulation patterns of anion $[Zn_4O(OCOCHCH_3)_6O_2]^{(-)}$ and cation $[Zn_4O(OCOCHCH_3)_5]^{(+)}$ theorized from $Zn_4O(OCOCHCH_2)_6$ are shown in FIGS. 6, 7.

As shown in FIGS. 6, 7, the ASAP-MS spectrum has the same pattern as the simulation pattern. Further, the obtained experimental values 632.7715 and 735.7762 are very close to the estimated values which is 632.7707 for the cation $[Zn_4O(OCOCHCH_3)_5]^{(+)}$: $C_{15}H_{15}O_{11}Zn_4$ and 735.7740 for the anion $[Zn_4O(OCOCHCH_3)_6O_2]^{(-)}$: $C_{18}H_{18}O_{15}Zn_4$. In addition, the measured value of the zinc amount is 36.8 mass %, which is very close to the theoretical value 37.2 mass %. Based on these results, it can be confirmed that the above prepared first complex 3 is the compound represented by $Zn_4O(OCOCHCH_2)_6$.

The element analysis results show that the first complex 3 contains carbon in an amount of 30.72 mass % and hydrogen in an amount of 2.50 mass %. The differences between the analysis results and the estimated values were 0.01 mass % for the carbon amount and 0.08 mass % for the hydrogen amount. Since the atomic compositions are very close to the estimated values, it can be confirmed that the first complex ($Zn_4O(OCOCHCH_2)_6$) has a very high purity.

Figure 8:
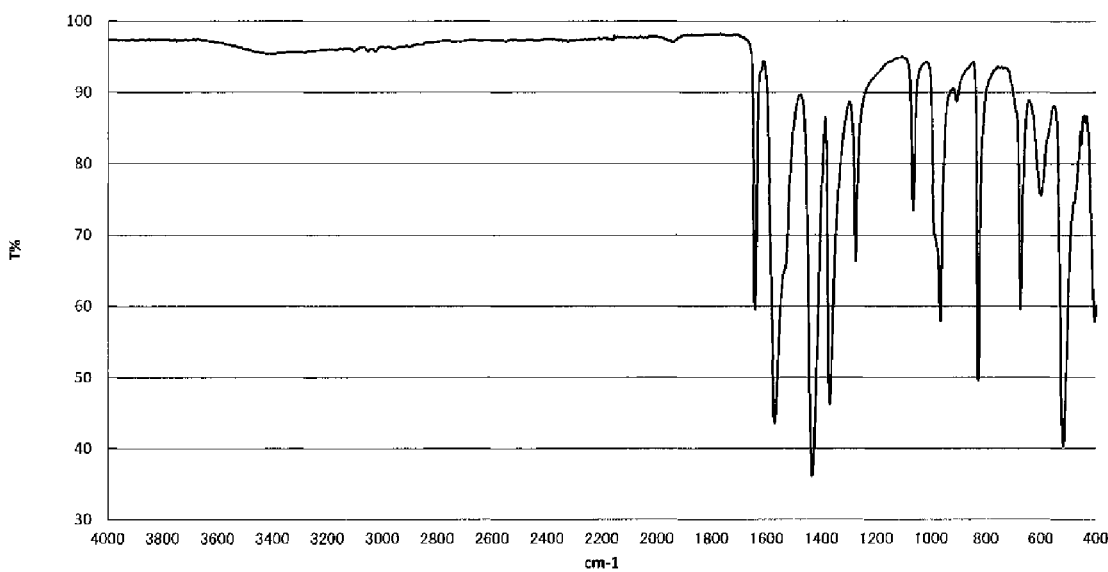
FIG. 8 shows IR spectrum of an intermediate complex obtained in the preparing process according to the present invention.
Figure 9:
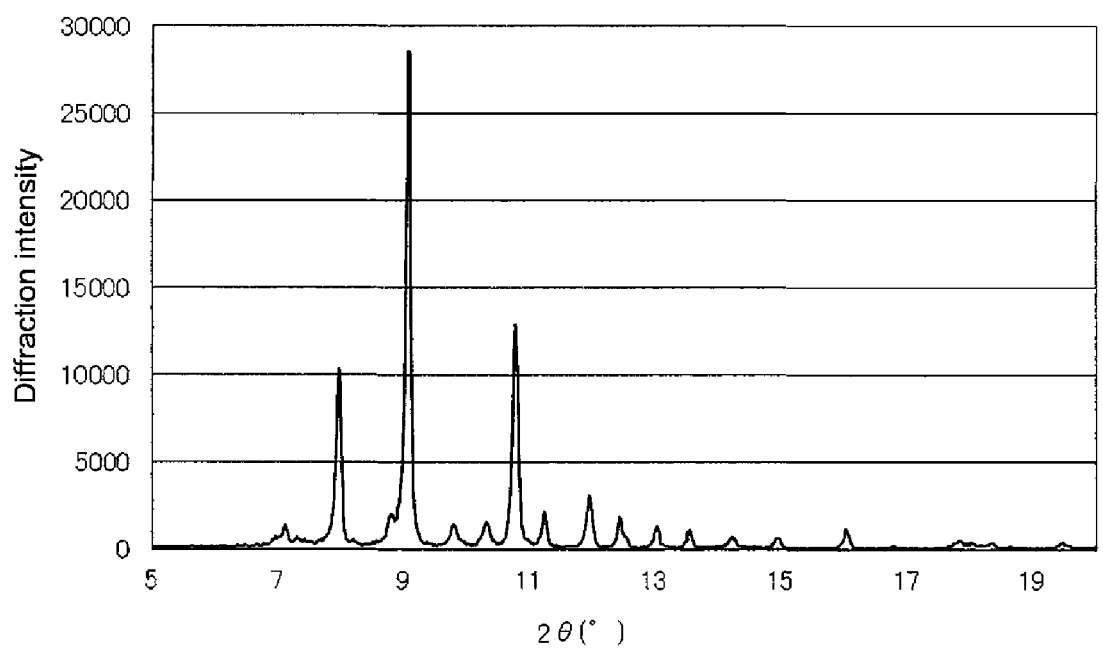
FIG. 9 shows X-ray diffraction spectrum of an intermediate complex obtained in the preparing process according to the present invention.

FIG. 8 shows IR spectrum of the first complex 3, and FIG. 9 shows X-ray diffraction spectrum of the first complex 3. Based on the IR spectrum, the absorption attributed to the vinyl group of acrylate and the absorption attributed to the vibration of $Zn_4O$ are confirmed. Further, it is also confirmed that the carboxylate group has a different coordination state from zinc diacrylate. Based on the X-ray diffraction spectrum, it is confirmed that the first complex 3 (zinc acrylate oxo cluster) has a different crystal structure from zinc diacrylate.

Figure 10:
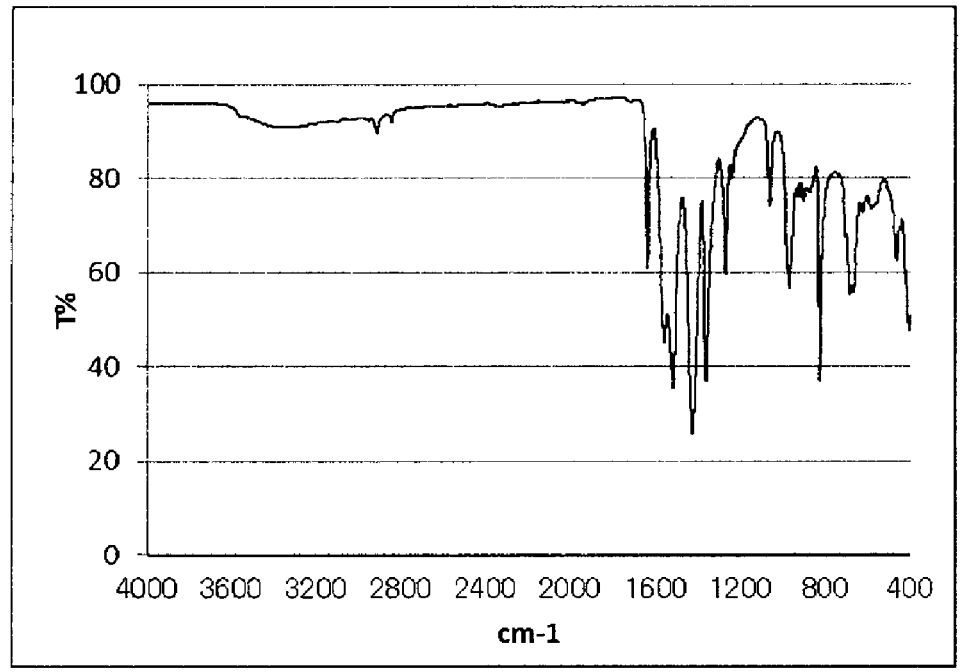
FIG. 10 shows IR spectrum of a preferable complex according to the present invention.
Figure 11:
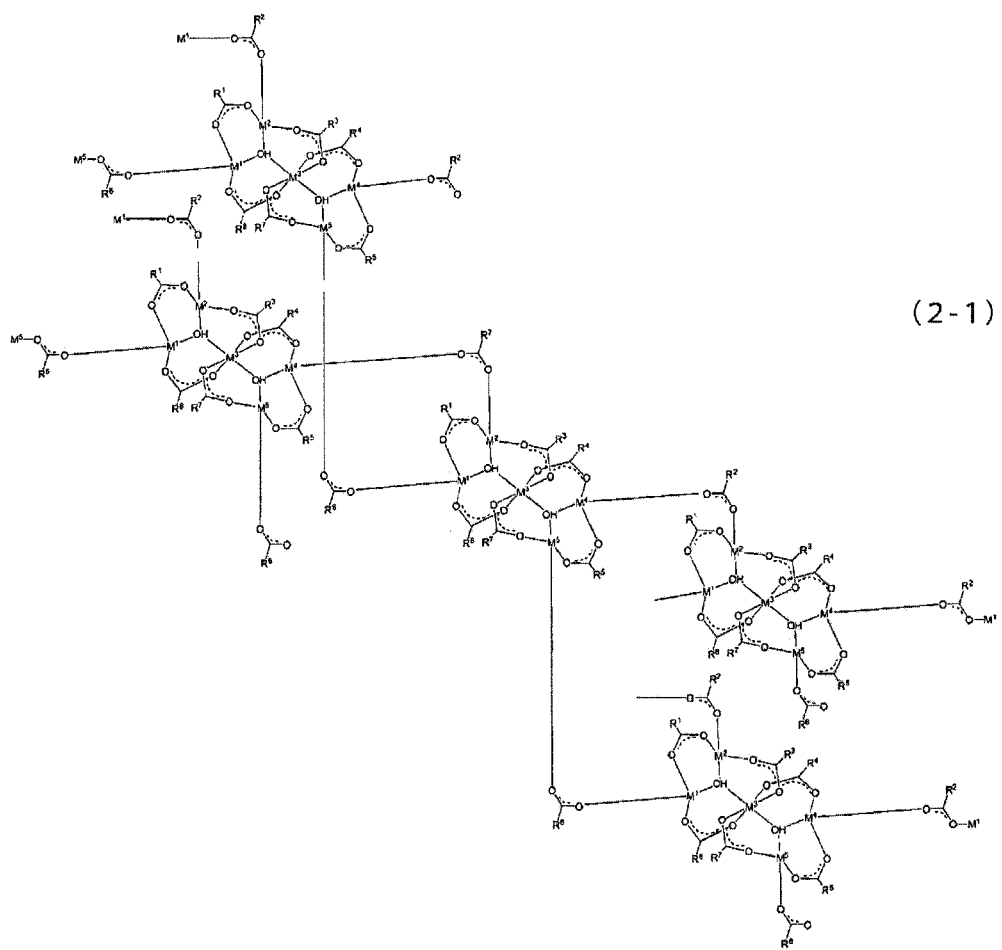
FIG. 11 shows a three dimensional structure of the assembled complex of the structural formula (2)
Figure 12:
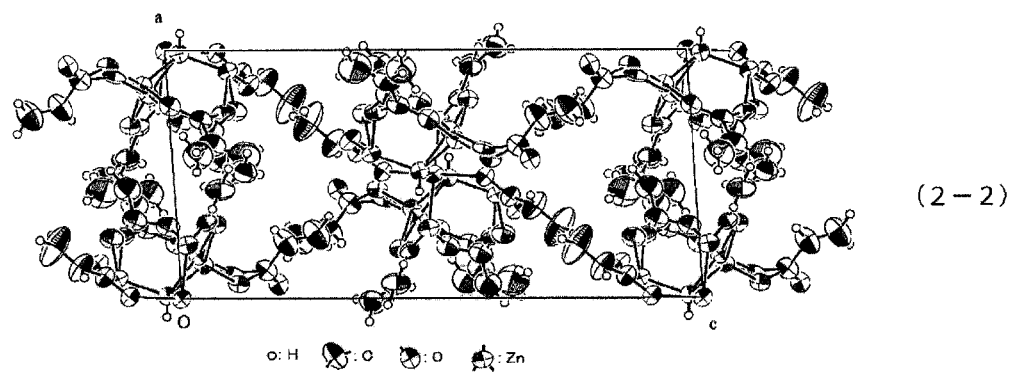
FIG. 12 shows an Oak ridge thermal-ellipsoid plot program of the crystal structure of the assembled complex.
Figure 13:
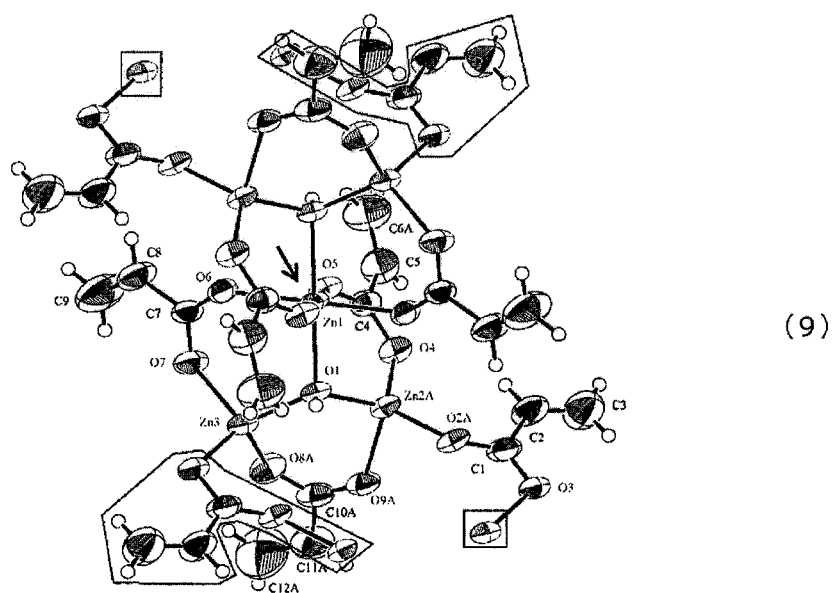
FIG. 13 shows an Oak ridge thermal-ellipsoid plot program of the crystal structure of the second complex 3 according to the inventive preparing example 3.

FIG. 10 shows IR spectrum of the second complex 3 obtained in the inventive preparing example 3.

IR spectrum peak: 413 $cm^{-1}$, 469 $cm^{-1}$, 688 $cm^{-1}$, 829 $cm^{-1}$, 972 $cm^{-1}$, 1068 $cm^{-1}$, 1274 $cm^{-1}$, 1372 $cm^{-1}$, 1435 $cm^{-1}$, 1522 $cm^{-1}$, 1568 $cm^{-1}$, 1644 $cm^{-1}$.

Based on the IR spectrum of the second complex 3 obtained in the inventive preparing example 3, the absorption attributed to the vinyl group of acrylate and the absorption attributed to the vibration of $(HO)Zn_3$ are confirmed. Further, two types of absorption attributed to the vibration of the carboxylate groups which have different coordination states from each other are confirmed.

The second complex 3 obtained in the inventive preparing example 3 was analyzed by single crystal X-ray diffraction to determine the structure. As a result, it has been found that the second complex 3 has the following structure. The arrow shows the symmetrical center of this structure and the part enclosed by the line shows a part of the adjacent molecule which mutually interacts.

Based on EDTA titration and mass analysis, it is confirmed that the second complex 3 has an atomic composition ratio and zinc content which correspond to those of $Zn_5(OCOCHCH_2)_8(OH)_2$ and thus is the metal cluster of the present invention.

Further, XRD result (FIG. 2) shows that the second complex 3 has a different crystal structure from zinc acrylate, and FT-IR shows the existence of a vinyl group and an absorption attributed to the vibration of $(HO)Zn_3$, and the absorption attributed to the vibration of two different kinds of acrylates. Accordingly, it is confirmed that $Zn_5(OCOCHCH_2)_8(OH)_2$ was prepared in a high purity.

Comparative Preparing Example 1

Zinc acrylate (2.0 g, 9.6 mmol) and 140 ml of toluene as a solvent were charged into a reaction vessel to dissolve or disperse zinc acrylate in toluene. Into the reaction liquid, 3 ml of water and 20 mg of 4-methoxyphenol as a polymerization inhibitor were further added as additives. The reaction liquid was stirred for 12 hours while refluxing toluene at 110° C. After finishing the reaction, the reaction liquid was filtered to obtain a filtrate. The filtration residue had a mass of 1.77 g (88.5%). The obtained filtrate was concentrated to obtain a concentrate (0.21 g, 10.5%). The concentrate was analyzed and no target product was confirmed.

Comparative Preparing Example 2

The reaction was conducted by the same method as the comparative preparing example 1 except that chloroform was used as the solvent and the reaction liquid was stirred while refluxing chloroform at 60° C. The filtration residue had a mass of 0.24 g (12%). The obtained filtrate was concentrated to obtain a concentrate (1.44 g, 72%). The concentrate was analyzed and no target product was confirmed.

Comparative Preparing Example 3

The reaction was conducted by the same method as the comparative preparing example 1 except that 140 ml of 1,2-dichlorobenzene was used as the solvent and the reaction liquid was stirred at 110° C. There was no insoluble substance in the reaction liquid. The obtained filtrate failed to be concentrated, and the target product failed to be obtained.

Comparative Preparing Example 4

The reaction was conducted by the same method as the comparative preparing example 1 except that 140 ml of propyl acetate was used as the solvent and the reaction liquid was stirred while refluxing propyl acetate at 100° C. The filtration residue had a mass of 1.71 g (85.5%). The target product failed to be obtained.

Comparative Preparing Example 5

The reaction was conducted by the same method as the comparative preparing example 1 except that 140 ml of acetone was used as the solvent and the reaction liquid was stirred while refluxing acetone at 56° C. The filtration residue had a mass of 0.26 g (13%). The obtained filtrate was concentrated to obtain a concentrate (1.54 g, 77%). The concentrate was analyzed and no target product was confirmed.

Comparative Preparing Example 6

The reaction was conducted by the same method as the comparative preparing example 1 except that 140 ml of N,N-dimethyl formamide (DMF) was used as the solvent and the reaction liquid was stirred at 100° C. There was no insoluble substance in the reaction liquid. The obtained filtrate failed to be concentrated, and the target product failed to be obtained.

Comparative Preparing Example 7

The reaction was conducted by the same method as the comparative preparing example 1 except that 140 ml of acetonitrile was used as the solvent and the reaction liquid was stirred while refluxing acetonitrile at 82° C. There was no insoluble substance in the reaction liquid. The obtained filtrate was concentrated to obtain a concentrate (1.8 g, 90%). The concentrate was analyzed and no target product was confirmed.

Comparative Preparing Example 8

The reaction was carried out by the same method as the comparative preparing example 1 except that 140 ml of dimethylsulfoxide (DMSO) was used as the solvent and the reaction liquid was stirred at 100° C. There was no insoluble substance in the reaction liquid. The obtained filtrate failed to be concentrated, and the target product failed to be obtained.

The preparing conditions and results of the comparative preparing examples 1 to 8 are summarized in Table 3.

Comparative Preparing Example 9

Zinc acrylate (5.02 g, 24 mmol) and 200 ml of toluene as a solvent were charged into a reaction vessel to dissolve or disperse zinc acrylate in toluene. Into the reaction liquid, 3 ml of water was further added as an additive. The reaction liquid was stirred for 2 hours while refluxing toluene at 110° C. After finishing the reaction, the reaction liquid was filtered to obtain a filtrate. The obtained filtrate was concentrated to obtain a concentrate (0.38 g, 7.6%). The concentrate was analyzed and no target product was confirmed.

Comparative Preparing Example 10

Zinc acrylate (2.00 g, 9.6 mmol) and 200 ml of toluene as a solvent were charged into a reaction vessel to dissolve or disperse zinc acrylate in toluene. Into the reaction liquid, 2 ml of water was further added as an additive. The reaction liquid was stirred for 2 hours while refluxing toluene at 110° C. After finishing the reaction, the reaction liquid was filtered to obtain a filtrate. The obtained filtrate was concentrated to obtain a concentrate (0.37 g, 18.6%). The concentrate was analyzed and no target product was confirmed.

Comparative Preparing Example 11

Zinc acrylate (2.01 g, 9.7 mmol) and 200 ml of toluene as a solvent were charged into a reaction vessel to dissolve or disperse zinc acrylate in toluene. Into the reaction liquid, 2 ml of water was further added as an additive. The reaction liquid was stirred for 1 hour at 90° C. After finishing the reaction, the reaction liquid was filtered to obtain a filtrate. The obtained filtrate was concentrated to obtain a concentrate (1.07 g, 53.2%). The concentrate was analyzed and no target product was confirmed.

Comparative Preparing Example 12

Zinc acrylate (2.04 g, 9.8 mmol) and 200 ml of toluene as a solvent were charged into a reaction vessel to dissolve or

TABLE 3

| Comparative preparing example | Material | | Additive | | Reaction solvent | | Reaction conditions | | Reaction product | | | | Note |
|---|---|---|---|---|---|---|---|---|---|---|---|---|---|
| | | | Water | 4-Methoxyphenol | Type | ml | Temperature (° C.) | Time (h) | Filtration residue | | Filtrate concentrate | | |
| | g | mmol | | | | | | | (g) | (%) | (g) | (%) | |
| 1 | ZDA 2.0 | 9.6 | 3 ml | 20 mg | Toluene | 140 | Reflux 110° C. | 12 | 1.77 | 88.5 | 0.21 | 10.5 | No target product generated |
| 2 | ZDA 2.0 | 9.6 | 3 ml | 20 mg | Chloroform | 140 | Reflux 60° C. | 12 | 0.24 | 12 | 1.44 | 72 | No target product generated |
| 3 | ZDA 2.0 | 9.6 | 3 ml | 20 mg | 1,2-Dichlorobenzene | 140 | 110° C. | 12 | No insoluble component | | Failed to be concentrated | | No target product generated |
| 4 | ZDA 2.0 | 9.6 | 3 ml | 20 mg | Propyl acetate | 140 | Reflux 100° C. | 12 | 1.71 | 85.5 | — | — | No target product generated |
| 5 | ZDA 2.0 | 9.6 | 3 ml | 20 mg | Acetone | 140 | Reflux 56° C. | 12 | 0.26 | 13.0 | 1.54 | 77 | No target product generated |
| 6 | ZDA 2.0 | 9.6 | 3 ml | 20 mg | DMF | 140 | 100° C. | 12 | No insoluble component | | Solid failed to be obtained | | No target product generated |
| 7 | ZDA 2.0 | 9.6 | 3 ml | 20 mg | Acetonitrile | 140 | Reflux 82° C. | 12 | No insoluble component | | 1.8 | 90 | No target product generated |
| 8 | ZDA 2.0 | 9.6 | 3 ml | 20 mg | DMSO | 140 | 100° C. | 12 | No insoluble component | | Failed to be concentrated | | No target product generated |

ZDA: zinc acrylate
Yield (%) = 100 × (value obtained by dividing each output by molecular weight of cluster)/(theoretical value (mole) of cluster estimated from raw materials)

disperse zinc acrylate in toluene. Into the reaction liquid, 0.5 ml of water was further added as an additive. The reaction liquid was stirred for 1 hour while refluxing toluene at 110° C. After finishing the reaction, the reaction liquid was filtered to obtain a filtrate. The obtained filtrate was concentrated to obtain a concentrate (1.67 g, 81.7%). The concentrate was analyzed and no target product was confirmed.

Comparative Preparing Example 13

Zinc acrylate (2.01 g, 9.7 mmol) and 200 ml of toluene as a solvent were charged into a reaction vessel to dissolve or disperse zinc acrylate in toluene. The reaction liquid was stirred for 1 hour while refluxing toluene at 110° C. After finishing the reaction, the reaction liquid was filtered to obtain a filtrate. The obtained filtrate was concentrated to obtain a concentrate (0.30 g, 14.8%). The concentrate was analyzed and no target product was confirmed.

Comparative Preparing Example 14

Zinc acrylate (2.08 g, 10 mmol) and 200 ml of toluene as a solvent were charged into a reaction vessel to dissolve or disperse zinc acrylate in toluene. Into the reaction liquid, 1 ml of water was further added as an additive. The reaction liquid was stirred for 2 hours while refluxing toluene at 110° C. After finishing the reaction, the reaction liquid was filtered to obtain a filtrate. The obtained filtrate was concentrated to obtain a concentrate (0.85 g, 41%). The concentrate was analyzed and no target product was confirmed.

Comparative Preparing Example 15

Zinc acrylate (10 g, 4.8 mmol) and 49 ml of toluene as a solvent were charged into a reaction vessel to dissolve or disperse zinc acrylate in toluene. The reaction liquid was stirred for 5 hours while refluxing toluene at 110° C. After finishing the reaction, the reaction liquid was filtered to obtain a filtrate. The obtained filtrate was concentrated to obtain a concentrate (0.26 g, 2.6%). The concentrate was analyzed and a polymer of zinc acrylate was confirmed.

Comparative Preparing Example 16

Zinc acrylate (10 g, 4.8 mmol) and 49 ml of toluene as a solvent were charged into a reaction vessel to dissolve or disperse zinc acrylate in toluene. The reaction liquid was stirred for 24 hours while refluxing toluene at 110° C. After finishing the reaction, the reaction liquid was filtered to obtain a filtrate. The obtained filtrate was concentrated to obtain a concentrate (0.08 g, 0.8%). The concentrate was analyzed and a polymer of zinc acrylate was confirmed.

Comparative Preparing Example 17

Zinc acrylate (10 g, 4.8 mmol) and 97 ml of toluene as a solvent were charged into a reaction vessel to dissolve or disperse zinc acrylate in toluene. The reaction liquid was stirred for 24 hours while refluxing toluene at 110° C. After finishing the reaction, the reaction liquid was filtered to obtain a filtrate. The obtained filtrate was concentrated to obtain a concentrate (0.03 g, 0.3%). The concentrate was analyzed and a polymer of zinc acrylate was confirmed.

Comparative Preparing Example 18

Zinc acrylate (10 g, 4.8 mmol) and 97 ml of xylene as a solvent were charged into a reaction vessel to dissolve or disperse zinc acrylate in xylene. The reaction liquid was stirred for 5 hours while refluxing xylene at 110° C. After finishing the reaction, the reaction liquid was filtered to obtain a filtrate. The obtained filtrate was concentrated to obtain a concentrate (0.19 g, 1.9%). The concentrate was analyzed and a polymer of zinc acrylate was confirmed.

The reaction conditions and results of the comparative preparing examples 9 to 18 are summarized in Table 4.

TABLE 4

| Comparative preparing example | Material | | Additive | Solvent | | Reaction conditions | | Filtrate concentrate | | Note |
|---|---|---|---|---|---|---|---|---|---|---|
| | | | Water | Type | ml | Temperature (° C.) | Time (h) | (g) | (%) | |
| | g | mmol | | | | | | | | |
| 9 | ZDA 5.02 | 24 | 3 ml | Toluene | 200 | Reflux 110° C. | 2 | 0.38 | 7.6 | No target product generated |
| 10 | ZDA 2.00 | 9.6 | 2 ml | Toluene | 200 | Reflux 110° C. | 2 | 0.37 | 18.6 | No target product generated |
| 11 | ZDA 2.01 | 9.7 | 2 ml | Toluene | 200 | 90° C. | 1 | 1.07 | 53.2 | No target product generated |
| 12 | ZDA 2.04 | 9.8 | 0.5 ml | Toluene | 200 | Reflux 110° C. | 1 | 1.67 | 81.7 | No target product generated |
| 13 | ZDA 2.01 | 9.7 | 0 | Toluene | 200 | Reflux 110° C. | 1 | 0.30 | 14.8 | No target product generated |
| 14 | ZDA 2.08 | 10.0 | 1 ml | Toluene | 200 | Reflux 110° C. | 1 | 0.85 | 41 | No target product generated |
| 15 | ZDA 10 | 4.8 | 0 | Toluene | 49 | Reflux 110° C. | 5 | 0.26 | 2.6 | Polymer of ZDA |
| 16 | ZDA 10 | 4.8 | 0 | Toluene | 49 | Reflux 110° C. | 24 | 0.08 | 0.8 | Polymer of ZDA |
| 17 | ZDA 10 | 4.8 | 0 | Toluene | 97 | Reflux 110° C. | 24 | 0.03 | 0.3 | Polymer of ZDA |
| 18 | ZDA 10 | 4.8 | 0 | Xylene | 97 | Reflux 110° C. | 5 | 0.19 | 1.9 | Polymer of ZDA |

ZDA: zinc acrylate

Yield (%) = 100 × (value obtained by dividing each output by molecular weight of cluster)/(theoretical value (mole) of cluster estimated from raw materials)

Comparative Preparing Example 19

Zinc oxide (30 g, 369 mmol) and 250 ml of dichloromethane were charged into a reaction vessel, and stirred at 0° C. A liquid obtained by dissolving acrylic acid (13.3 g, 184 mmol) in 125 ml of dichloromethane was added dropwise therein at a dropwise addition speed of 2.5 ml/min. After the dropwise addition, the reaction liquid was heated to 40° C. and stirred for 3 hours, and then the reaction was finished. The obtained reaction liquid was filtered to remove the insoluble precipitate in the solvent. 300 ml of hexane was added into the filtrate, and concentration under reduced pressure was performed until the liquid amount was reduced to about one-fourth, to obtain a concentrate. The concentrate was analyzed and no target product was confirmed.

Comparative Preparing Example 20

In a reaction vessel, a liquid obtained by dissolving or dispersing zinc oxide (2.5 g, 31 mmol) and zinc acrylate (19.1 g, 92 mmol) in 375 ml of dichloromethane was stirred at 40° C. for 3 hours. It is noted that the solvent was refluxed. The obtained reaction liquid was filtered to remove the insoluble precipitate in the solvent. 300 ml of hexane was added into the filtrate, and concentration under reduced pressure was performed until the liquid amount was reduced to about one-fourth, to obtain a precipitate. The precipitate was removed by filtration, and the filtrate was dried to obtain a concentrate (1.82 g). The concentrate was acrylic acid oxo cluster, and no acrylic acid hydroxo cluster was confirmed.

The preparing conditions and results of the comparative preparing examples 19 to 20 are summarized in Table 5.

TABLE 5

| Comparative preparing example | Compounds (4) or (6) (g) | (mmol) | Metal oxide (5) (g) | (mmol) | Compounds (4), (6)/metal oxide (5) (molar ratio) | Solvent (ml) | Temperature (° C.) | Time (h) | Water (ml) | Output (g) | Yield (%) |
|---|---|---|---|---|---|---|---|---|---|---|---|
| 19 | AA 13.3 | 184 | ZnO 30 | 369 | 1:2 | Dichloromethane 250 + 125 ml | 0° C. to 40° C. | 3 | 0.75 | 0.24 | No target product generated |
| 20 | ZDA 19 | 92 | ZnO 2.5 | 31 | 3:1 | Dichloromethane 375 ml | 40° C. | 3 | None | 1.82 | No target product generated |

AA: acrylic acid,
ZDA: zinc acrylate
Yield (%) = 100 × (value obtained by dividing each output by molecular weight of cluster)/(theoretical value (mole) of cluster estimated from raw materials)

[Preparation of Rubber Composition]

Materials having the formulations shown in Table 6 were kneaded to prepare rubber compositions.

TABLE 6

| | | Rubber composition | 1 | 2 |
|---|---|---|---|---|
| Formulation (parts by mass) | (a) | BR730 | 100 | 100 |
| | (b) | Zinc acrylate hydroxo cluster | 20.5 | — |
| | | ZN-DA90S | — | 19.7 |
| | (d) | Zinc oxide | 2.69 | 5 |
| | (c) | Dicumyl peroxide | 0.8 | 0.8 |
| Crosslinking component | | Acrylate (parts by mass) | 12.1 | 12.1 |
| | | Zinc (parts by mass) | 9.6 | 9.6 |
| Evaluation | Molding conditions | Temperature (° C.) | 170 | 170 |
| | | Time (min) | 20 | 20 |

TABLE 6-continued

| | Rubber composition | 1 | 2 |
|---|---|---|---|
| Slab properties | Shore C hardness | 63.5 | 62.6 |
| | Lupke type rebound resilience (%) | 72.9 | 67.2 |

The materials used in Table 6 are shown as follows.

BR730: high-cis polybutadiene (amount of cis-1,4 bond=96 mass %, amount of 1,2-vinyl bond=1.3 mass %, Moony viscosity ($ML_{1+4}$ (100° C.)=55, molecular weight distribution (Mw/Mn)=3) available from JSR Corporation Zinc acrylate hydroxo cluster: Second complex 3 obtained in the inventive preparing example 3

ZN-DA90S: zinc acrylate (a product coated with zinc stearate in an amount of 10 mass %) available from Nisshoku Techno Fine Chemical Co., Ltd.

Zinc oxide: "Ginrei R" available from Toho Zinc Co., Ltd.

Dicumyl peroxide: "Percumyl (register trademark) D" available from NOF Corporation Table 6 shows the hardness and rebound resilience of the slab formed from the rubber composition. It is apparent that the crosslinked rubber molded products (slabs) using the complex according to the present invention each exhibits high resilience performance, thus the usefulness of the complex according to the present invention as a co-crosslinking agent is confirmed.

A crosslinked rubber molded product having an excellent resilience performance can be obtained by using the rubber composition of the present invention. Thus, the rubber composition of the present invention can be used in sports goods such as golf balls and tennis balls.

This application is based on Japanese Patent Applications No. 2016-250052 filed on Dec. 22, 2016, and No. 2017-129264 filed on Jun. 30, 2017, the content of which is hereby incorporated by reference.

The invention claimed is:

1. A complex of formula (1):

$$((RCOO)_8M_5(OH)_2)_n \qquad (1)$$

wherein in the formula (1), M is zinc, and R is —CH=$CH_2$ or —C($CH_3$)=$CH_2$.

2. The complex according to claim 1, wherein n is an integer of 1 or more, and the complex is a complex of structural formula (2):

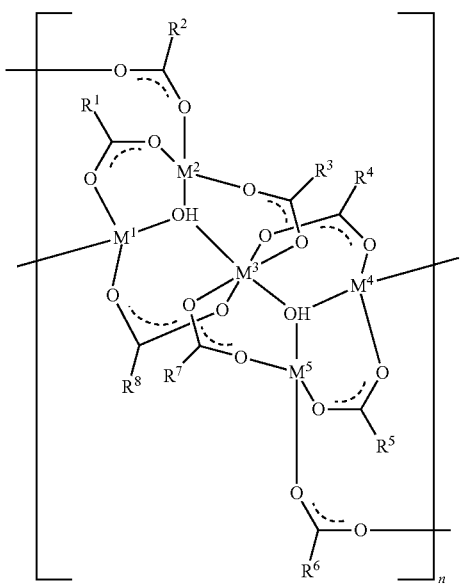

(2)

wherein in the formula (2), $M^1$ to $M^5$ are zinc, and $R^1$ to $R^8$ are —CH=CH$_2$ or —C(CH$_3$)=CH$_2$.

3. The complex according to claim 2, wherein n in the formula (2) is 1, and the complex of the structural formula (2) has a structure of structural formula (3):

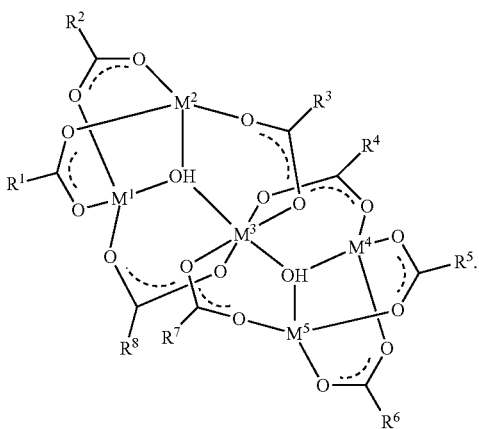

(3)

4. A process of preparing a complex, comprising a step of reacting a compound of formula (4) with a metal oxide of formula (5) in a solvent in the presence of water:

[M$^6$(RCOO)$_x$]·yH$_2$O     (4)

M$^7_a$O$_b$     (5)

wherein in the formula (4), M$^6$ is zinc, R is —CH=CH$_2$ or —C(CH$_3$)=CH$_2$, x is two, y is zero; and in the formula (5), M$^7$ is zinc, a is one, and b is one, wherein the prepared complex is a complex of formula (1).

5. The process of preparing a complex according to claim 4 wherein a molar ratio ((4)/(5)) of the compound of the formula (4) to the metal oxide of the formula (5) ranges from 3/2 to 5/1.

6. The process of preparing a complex according to claim 4, wherein dichloromethane is used as the solvent.

7. The process of preparing a complex according to claim 4, wherein the reaction is performed at a temperature ranging from −20° C. to 100° C.

8. A process of preparing a complex, comprising a step of reacting a compound of formula (4) with a metal oxide of formula (5) in a solvent to obtain a first complex, and a step of reacting the first complex with water to obtain a second complex:

[M$^6$(RCOO)$_x$]·yH$_2$O     (4)

M$^7_a$O$_b$     (5)

wherein in the formula (4), M$^6$ is zinc, R is —CH=CH$_2$ or —C(CH$_3$)=CH$_2$, x is two, y is zero; and in the formula (5), M$^7$ is zinc, a is one, and b is one, wherein the prepared second complex is a complex of formula (1).

9. The process of preparing a complex according to claim 8, wherein the reaction of the first complex with water is performed by exposing the first complex under an atmosphere having a relative humidity of 50% or more.

10. A process of preparing a complex, comprising a step of reacting a carboxylic acid of formula (6) with a metal oxide of formula (5) in a solvent:

RCOOH     (6)

M$^7_a$O$_b$     (5)

wherein in the formula (6), R is —CH=CH$_2$ or —C(CH$_3$)=CH$_2$, and in the formula (5), M$^7$ is zinc, a is one, and b is one, wherein the prepared complex is zinc, a is one, and b is one, and b is one, wherein the prepared complex is a complex of formula (1).

11. The process of preparing a complex according to claim 10, wherein a molar ratio ((6)/(5)) of the carboxylic acid of the formula (6) to the metal oxide of the formula (5) is more than 1/2 and 7/4 or less.

* * * * *